US008633300B2

(12) United States Patent
Ostergaard et al.

(10) Patent No.: US 8,633,300 B2
(45) Date of Patent: Jan. 21, 2014

(54) SELECTIVE REDUCTION AND DERIVATIZATION OF ENGINEERED PROTEINS COMPRISING AT LEAST ONE NON-NATIVE CYSTEINE

(75) Inventors: Henrik Ostergaard, Lyngby (DK); Anders Klarskov Petersen, Naerum (DK)

(73) Assignee: Novo Nordisk Healthcare AG, Zurich (CH)

( * ) Notice: Subject to any disclaimer, the term of this patent is extended or adjusted under 35 U.S.C. 154(b) by 726 days.

(21) Appl. No.: 11/917,772

(22) PCT Filed: Jun. 19, 2006

(86) PCT No.: PCT/EP2006/063310
§ 371 (c)(1),
(2), (4) Date: Dec. 17, 2007

(87) PCT Pub. No.: WO2006/134173
PCT Pub. Date: Dec. 21, 2006

(65) Prior Publication Data
US 2008/0200651 A1    Aug. 21, 2008

Related U.S. Application Data

(60) Provisional application No. 60/692,315, filed on Jun. 20, 2005.

(30) Foreign Application Priority Data

Jun. 17, 2005  (EP) .................................. 05105362

(51) Int. Cl.
*A61K 35/14* (2006.01)
*C07K 1/00* (2006.01)

(52) U.S. Cl.
USPC .......................................... 530/384; 530/402

(58) Field of Classification Search
USPC ................................. 530/384, 402
See application file for complete search history.

(56) References Cited

U.S. PATENT DOCUMENTS

| 5,166,322 | A | 11/1992 | Shaw et al. |
| 5,766,897 | A | 6/1998 | Braxton |
| 5,969,040 | A | 10/1999 | Hallahan et al. |
| 6,806,063 | B2 * | 10/2004 | Pedersen et al. ............. 435/69.1 |
| 7,199,223 | B2 | 4/2007 | Bossard et al. |
| 2003/0044908 | A1 * | 3/2003 | Persson ........................ 435/69.1 |
| 2006/0040856 | A1 | 2/2006 | DeFrees et al. |
| 2009/0252720 | A1 | 10/2009 | Ostergaard et al. |

FOREIGN PATENT DOCUMENTS

| EP | 863154 | 9/1998 |
| EP | 775711 | 3/2003 |
| EP | 1481985 | 12/2004 |
| JP | H04-504801 A | 8/1992 |
| JP | 2002/534119 A | 10/2002 |
| JP | 2004/508014 A | 3/2004 |
| JP | 2004516300 A | 6/2004 |
| JP | 2004-529640 A | 9/2004 |
| JP | 2007-502887 A | 2/2007 |
| SE | 9501285 | 4/1995 |
| WO | 90/12874 A2 | 11/1990 |
| WO | WO 93/08842 | 5/1993 |
| WO | WO 94/12219 * | 6/1994 |
| WO | WO 01/58935 | 8/2001 |
| WO | WO 02/50099 | 6/2002 |
| WO | 02/068455 A2 | 9/2002 |
| WO | WO 02/077218 | 10/2002 |
| WO | WO 2004/101597 | 11/2004 |
| WO | WO 2004/101740 | 11/2004 |
| WO | WO 2005/001025 | 1/2005 |
| WO | WO 2005/003171 | 1/2005 |
| WO | 2005/019395 A1 | 3/2005 |
| WO | 2005/024006 A2 | 3/2005 |
| WO | 2005/033307 A1 | 4/2005 |
| WO | WO 2006/005058 | 1/2006 |
| WO | WO 2006/018204 | 2/2006 |
| WO | 2006/053299 A2 | 5/2006 |
| WO | WO 2006/103298 | 10/2006 |
| WO | 2006/134173 A2 | 12/2006 |

OTHER PUBLICATIONS

Ostergaard et al. "Monitoring disulfide bond formation in the eukaryotic cytosol", The Journal of Cell Biology, 2004, 166(3):337-345.*
Lundstrom-Ljung, J. et al., Glutaredoxin Accelerates Glutathione-dependent Folding of Reduced Ribonuclease A Together with protein Disulfide-isomerase, J. Biological Chemistry, vol. 270 (14), pp. 7822-28 (1995).
Higashi, S. et al., Conformation of Factor VIIa Stabilized by a Labile Disulfide Bond (Cys-310-Cys-329) in the Protease Domain is Essential for Interaction with Tissue Factor, J. Biological Chemistry, vol. 272 (41), pp. 25724-30 (1997).
Wang, E.C.W. et al., The role of Cys191-Cys220 disulfide bond in trypsin: new targets for engineering substrate specificity, Protein Engineering, vol. 10 (4), pp. 405-11 (1997).
Gilbert, Hiram F., Thiol/Disulfide Exchange Equilibria and Disulfide Bond Stability, Methods in Enzymology, vol. 251, pp. 8-28 (1995).
Xiao, R. et al., Catalysis of Thiol/Disulfide Exchange, J. Of Biological Chemistry, vol. 280 (22), pp. 21099-106 (2005).
Burns, J.A. et al., Selective Reduction of Disulfides by Tris(2-carboxyethl)phosphine, J. Organic Chemeistry, vol. 56, pp. 2648-50 (1991).
Hoffman and Monroe, Thrombosis and Haemostasis, 2001, vol. 85, pp. 958-965.
Schmidt et al., Trends in Cardiovascular Medicine, 2003, vol. 13, pp. 39-45.
Di Scipio et al., Journal of Clinical Investigation Activation of Human Factor IX (Christmas Factor), 1978, vol. 61, pp. 1528-1538.
Swedish Patent SE 9501285 with manual English language translation, Apr. 6, 1995.

(Continued)

*Primary Examiner* — Suzanne M Noakes
(74) *Attorney, Agent, or Firm* — Jianjie Hu

(57) ABSTRACT

The present invention relates to method for selective reduction and derivatization of recombinantly prepared engineered proteins comprising at least one non-native cysteine, wherein the reduction reaction is conducted in the presence of a redox buffer or in the presence of a triarylphosphine reducing agent.

12 Claims, 9 Drawing Sheets

(56) References Cited

OTHER PUBLICATIONS

Autin .L et al. Molecular models of the procoagulant Factor VIIIa-Factor IXa complex, Journal of Thrombosis and Haemostasis, 2005, vol. 3: 2044-2056.

Begbie ME et al. An important role for the activation peptide domain in controlling factor IX levels in the blood of haemophilia B mice. Thromb Haemost, 2005, 94(6), 1138-1147.

Brandstetter H. et al., X-ray structure of clotting factor IXa: active site and module structure related to Xase activity and hemophilia B. 1995, PNAS 92, 9796-9800.

Chen, S.W.W. et al., Model of a ternary complex between activated factor VII, tissue factor and factor IX, Thrombosis and Haemostasis, 2002, vol. 88, Issue 1,; pp. 74-82.

Greenland William E. P. et al., Water-Soluble Phosphines for Direct Labeling of Peptides with Technetium and Rhenium: Insights from Electrospray Mass Spectrometry, Bioconjugate Chemistry, 2005, vol. 16(4), 939-948.

Hopfner K.P. et al., Coagulation factor IXa: the relaxed conformation of Tyr99 blocks substrate binding, Structure with Folding & design, 1999, vol. 7 pp. 989-996.

Fernandes A et al. Glutaredoxins: Glutathione-Dependent Redox Enzymes with Functions Far Beyond a Simple Thioredoxin Backup System, Antioxidants & Redox Signaling, 2004, vol. 6, No. 1, pp. 63-74. Other.

\* cited by examiner

SEQUENCE LISTING

```
<160> NUMBER OF SEQ ID NOS: 6

<210> SEQ ID NO 1
<211> LENGTH: 32
<212> TYPE: DNA
<213> ORGANISM: Artificial Sequence
<220> FEATURE:
<223> OTHER INFORMATION: DNA primer

<400> SEQUENCE: 1
gggccgccca tggtatct caagaaacta tc                                    32

<210> SEQ ID NO 2
<211> LENGTH: 35
<212> TYPE: DNA
<213> ORGANISM: Artificial Sequence
<220> FEATURE:
<223> OTHER INFORMATION: DNA primer

<400> SEQUENCE: 2
gcccgggctc gagatttgca agaataggtt ctaac                               35

<210> SEQ ID NO 3
<211> LENGTH: 40
<212> TYPE: DNA
<213> ORGANISM: Artificial Sequence
<220> FEATURE:
<223> OTHER INFORMATION: DNA primer

<400> SEQUENCE: 3
gccgccggca tgaagcta tacatttacg atcactgccc                            40

<210> SEQ ID NO 4
<211> LENGTH: 46
<212> TYPE: DNA
<213> ORGANISM: Artificial Sequence
<220> FEATURE:
```

```
<223> OTHER INFORMATION: DNA primer

<400> SEQUENCE: 4
ccgccgccct cgagaatcgc cattgatgat aacaaattga tttgtg        46

<210> SEQ ID NO 5
<211> LENGTH: 32
<212> TYPE: DNA
<213> ORGANISM: Artificial Sequence
<220> FEATURE:
<223> OTHER INFORMATION: DNA primer

<400> SEQUENCE: 5
gtttagggct gcatgcgagt atggacagta cg        32

<210> SEQ ID NO 6
<211> LENGTH: 32
<212> TYPE: DNA
<213> ORGANISM: Artificial Sequence
<220> FEATURE:
<223> OTHER INFORMATION: DNA primer

<400> SEQUENCE: 6
cgtactgtcc atactcgcat gcagccctaa ac        32
```

SELECTIVE REDUCTION AND DERIVATIZATION OF ENGINEERED PROTEINS COMPRISING AT LEAST ONE NON-NATIVE CYSTEINE

CROSS-REFERENCE TO RELATED APPLICATIONS

This application is a 35 U.S.C. § 371 national stage application of International Patent Application PCT/EP2006/063310 (published as WO 2006/134173), filed Jun. 19, 2006, which claims priority of European Patent Application 05105362.7, filed Jun. 17, 2005. This application further claims priority under 35 U.S.C. § 119 of U.S. Provisional Application 60/692,315, filed Jun. 20, 2005.

FIELD OF THE INVENTION

The present invention relates to method for selective reduction and derivatization of recombinantly prepared engineered proteins comprising at least one non-native cysteine (e.g. coagulation factors or proteins of the trypsin family of serine proteases), wherein the reduction reaction is conducted in the presence of a redox buffer or in the presence of a triarylphosphine reducing agent.

BACKGROUND OF THE INVENTION

Coagulation factor VIIa is the key initiator of haemostasis. It is a 50-kDa plasma protein with a functional circulatory half life around 1-3 hours. The mature protein contains a total of 24 cysteine residues paired in 12 disulfide bondings. Of these, the disulfide bond bridging Cys340 and Cys368 in the protease domain is highly labile and readily reduced by even low concentrations of commonly used reducing agents such as β-mercaptoethanol, see Higashi (1997). Cys340-Cys368 (or Cys191-Cys220 according to chymotrypsin numbering) is highly conserved in the trypsin family of serine proteases including coagulation factors II, IX, X, XI and protein C, see Wang (1997). It forms part of the wall of the $S_1$ binding pocket and in FVIIa reduction of the disulfide bond results in a loss of amidolytic activity, see Higashi (1997).

Covalent modification, e.g. by PEGylation or lipid attachment, has been successfully applied on several protein-based pharmaceutics to improve their pharmacokinetic and pharmacodynamic profiles. Conjugation via native or engineered cysteines provides an attractive means of site-specific modification due to the rarity of this amino acid on the surface of proteins, particularly those secreted by the cell, as well as the high selectivity of the thiol-coupling chemistry.

Native Factor VIIa contains 24 cysteine residues and disulfide bridges are established between the following cysteine residues: C17 and C22, C50 and C61, C55 and C70, C72 and C81, C91 and C102, C98 and C112, C114 and C127, C135 and C262, C159 and C164, C178 and C194, C310 and C329, and between C340 and C368.

The lack of free thiols in native Factor VIIa has led to the proposal that prolongation of the circulatory half life might be achieved by modification, e.g. PEGylation, of engineered solvent-exposed cysteines, see, e.g. WO 02/077218 A1 and WO 01/58935 A2.

Hence, WO 01/58935 A2 discloses Factor VII polypeptide conjugates with non-polypeptide moieties and their preparation. It is, i.a., suggested that the non-polypeptide moiety is conjugated to the Factor VII polypeptide via a cysteine. Similarly, WO 02/077218 A1 discloses Factor VII polypeptide conjugates with chemical groups and their preparation. It is, i.a., suggested that the chemical group is conjugated to the Factor VII polypeptide via a cysteine.

In practice, however, this approach is somewhat complicated by the fact that introduced cysteines in predominant portions of the Factor VII polypeptide are found as mixed disulfides with low-molecular weight thiol compounds such as glutathione (γ-glutamyl-cysteinylglycine), cysteine, and homocysteine (see FIG. 1) when the polypeptide is prepared by recombinant techniques, thereby preventing subsequent chemical conjugation via the thiol groups of the cysteines. Thus, there is a need for methods in which mixed disulfides of such cysteines and low-molecular weight thiols can be chemically reduced with preservation of the native disulfide bonds.

SE 9501285A discloses a process for the in vitro production of appropriately folded, biologically active disulfide-crosslinked proteins using a mixture of a protein disulfide oxidoreductase (e.g. protein disulfide isomerase (PDI)), a glutaredoxin and a redox buffer. The reference is focused on cysteines involved in intramolecular disulfide bonds.

BRIEF DESCRIPTION OF THE INVENTION

In view of the above-mentioned obstacles with respect to chemical conjugation via thiol groups of cysteines not involved in intramolecular disulfide bonds of proteins prepared by recombinant techniques, the present invention now provides the use of a defined redox buffer mixture (e.g. in combination with a thiol-disulfide redox catalyst) or a triarylphosphine to selectively reduce the mixed disulfide bond between low-molecular weight thiols and an engineered protein comprising at least one non-native cysteine, e.g. a coagulation factor or a protein of the trypsin family of serine proteases, with such engineered or native cysteines. Following selective reduction of the mixed disulfide, the free cysteine can then be modified by conjugation using thiol-coupling chemistry on the protein as known to people skilled in the art.

Chemical conjugation via engineered or native cysteines offers the choice of targeted modification of proteins yielding a single homogenous product. However, in cases where the cysteine is conjugated to a low-molecular weight thiol and the protein contains labile intramolecular disulfide bonds this strategy is not feasible. The present invention enables selective removal of the low-molecular weight thiol moiety preparing the liberated cysteine for subsequent chemical modification.

Hence, one aspect of the present invention relates to a method for selective reduction of an engineered protein in its active conformation comprising at least one non-native cysteine, e.g. a coagulation factor or a protein of the trypsin-family of serine proteases, said protein comprising one or more cysteine moieties conjugated through a disulfide bridge to a low-molecular weight thiol (RS-Cys), said moiety/moieties not being involved in intramolecular S—S bridges (Cys-S-S-Cys) when the protein is in its active form, the method comprising the step of allowing the low-molecular weight thiol-conjugated protein to react with a mixture comprising a redox buffer under non-denaturing conditions.

Another aspect of the present invention relates to a method for selective reduction of an engineered protein in its active conformation comprising at least one non-native cysteine, e.g. a coagulation factor or a protein of the trypsin-family of serine proteases, said protein comprising one or more cysteine moieties conjugated through a disulfide bridge to a low-molecular weight thiol (RS-Cys), said moiety/moieties not being involved in intramolecular S—S bridges (Cys-S-S-Cys) when the protein is in its active form, the method comprising the step of allowing the low-molecular weight thiol-conjugated protein to react with a mixture comprising a triarylphosphine reducing agent under non-denaturing conditions.

The term "selectively reduced" refers to the fact that a predominant portion, e.g. a fraction of 60% or more, or 80% or more, such as 90% or more, of the cysteine moieties conjugated through a disulfide bridge to a low-molecular weight thiol are reduced to liberate a cysteine moiety with a thiol group which is ready for conjugation with other groups, whereas predominant portion, e.g. 60% or more, or 80% or more, such as 90% or more, of other disulfide bonds (typically intramolecular disulfide bonds) are preserved so that the biological activity of the engineered protein is substantially preserved. In one embodiment, the protein is said to be "selectively reduced" if one or more non-native cysteine moieties are reduced in the protein, while the biological activity is substantially preserved, e.g. 60% or more, such as 80% or more, such as 90% or more of the activity is preserved as compared to the activity of non-reduced protein.

DETAILED DESCRIPTION OF THE INVENTION (A) Redox Buffer

As mentioned above, the present invention provides a method for selective reduction of an engineered protein in its active conformation comprising at least one non-native cysteine, e.g. a coagulation factor or a protein of the trypsin-family of serine proteases. The protein in question comprises one or more cysteine moieties conjugated through a disulfide bridge to a low-molecular weight thiol (RS-Cys), said moiety/moieties not being involved in intramolecular S—S bridges (Cys-S—-S-Cys) when the protein is in its active form, the method comprising the step of allowing the low-molecular weight thiol-conjugated protein to react with a mixture comprising a redox buffer under non-denaturing conditions.

When used herein, the term "redox buffer" is intended to mean a thiol/disulfide redox pair in a ratio that is sufficiently reducing to disrupt the protein-low-molecular weight thiol mixed disulfide(s) (RS-Cys) and at the same time sufficiently oxidizing to preserve the integrity of the native disulfide bonds in the protein.

Preferably, the redox buffer comprises a low molecular weight thiol/disulfide redox pair. By the term "low molecular weight" is meant that the thiol-form of the redox pair has a molecular weight of at the most 500 g/mol. Illustrative examples of such redox pairs are the ones selected from (i) reduced and oxidized glutathione and (ii) reduced and oxidized γ-glutamylcysteine, (iii) reduced and oxidized cysteinylglycine, (iv) reduced and oxidized cysteine, (v) reduced and oxidized N-acetylcysteine, (vi) cysteamine, and (vii) dihydrolipoamide/lipoamide, preferably from (i) reduced and oxidized glutathione.

Figure 2:
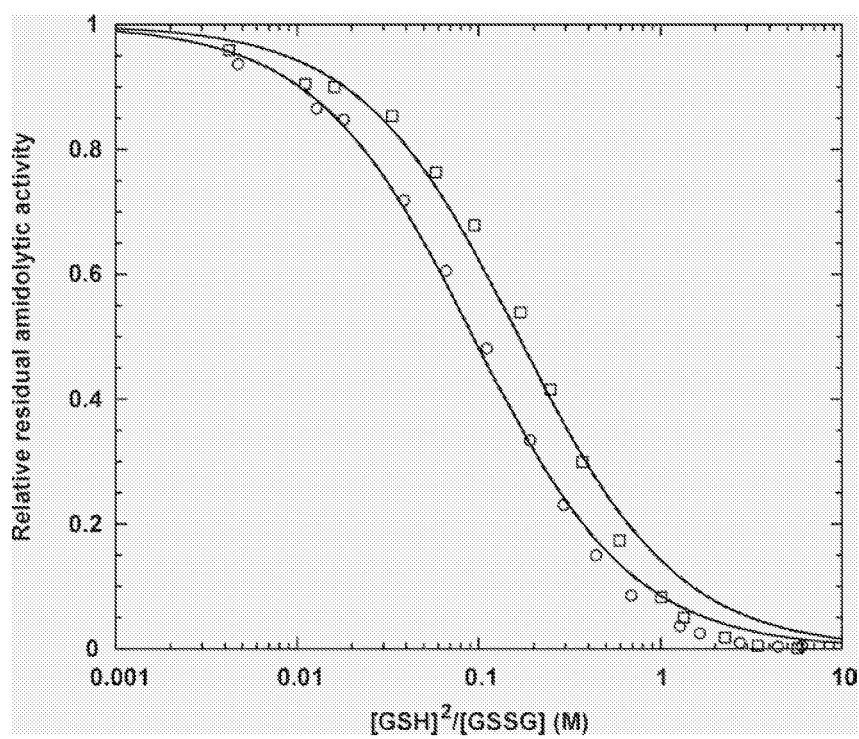
FIG. 2: Residual amidolytic activity of FVIIa incubated at pH 7 in the presence of varying concentrations of reduced and oxidized glutathione (given by the [GSH]$^2$/[GSSG] ratio), 1 μM yeast glutaredoxin 1 (yGrx1p), and either no (open circles) or 25 mM p-aminobenzamidine (open squares). All samples were allowed to equilibrate for 3.5 hrs at 30° C. before the amidolytic activity was measured. Amidolytic activities are normalized to 1 for fully active FVIIa.
Figure 3:
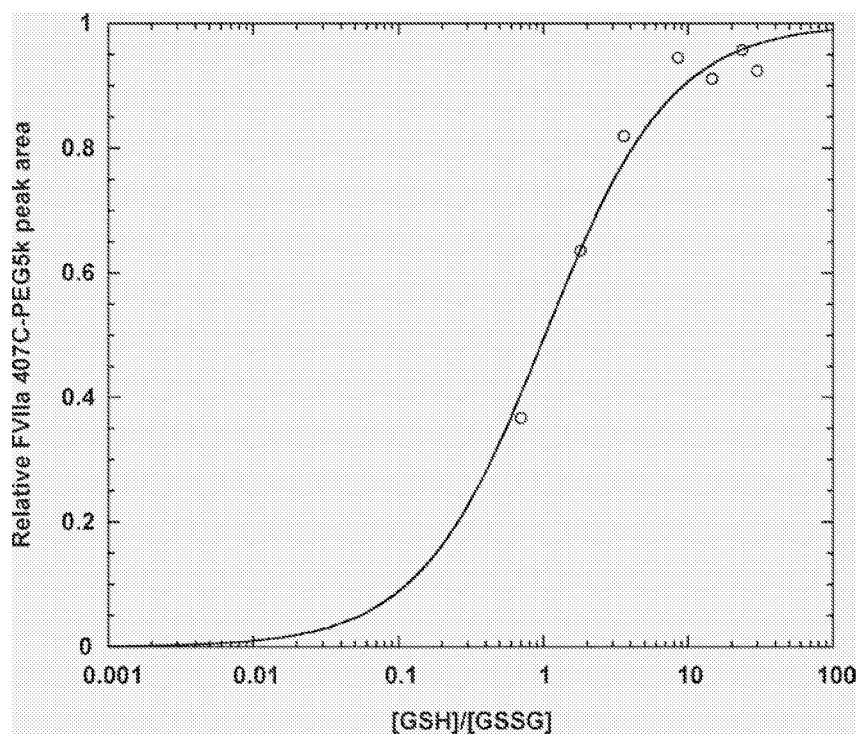
FIG. 3: Redox titration of the mixed-disulfide between FVIIa Cys407 and glutathione. FVIIa 407C was allowed to equilibrate in pH 7 buffer containing varying ratios of reduced and oxidized glutathione (given by the [GSH]/[GSSG] ratio) and 10 μM E. coli glutaredoxin 2 (Grx2). Following equilibration for 5 hrs at 30° C., free FVIIa 407C was detected and quantified by HPLC after alkylation with PEG5k-maleimide. Peak areas are normalized to 1 for fully 5k-PEGylated FVIIa.
Figure 4:
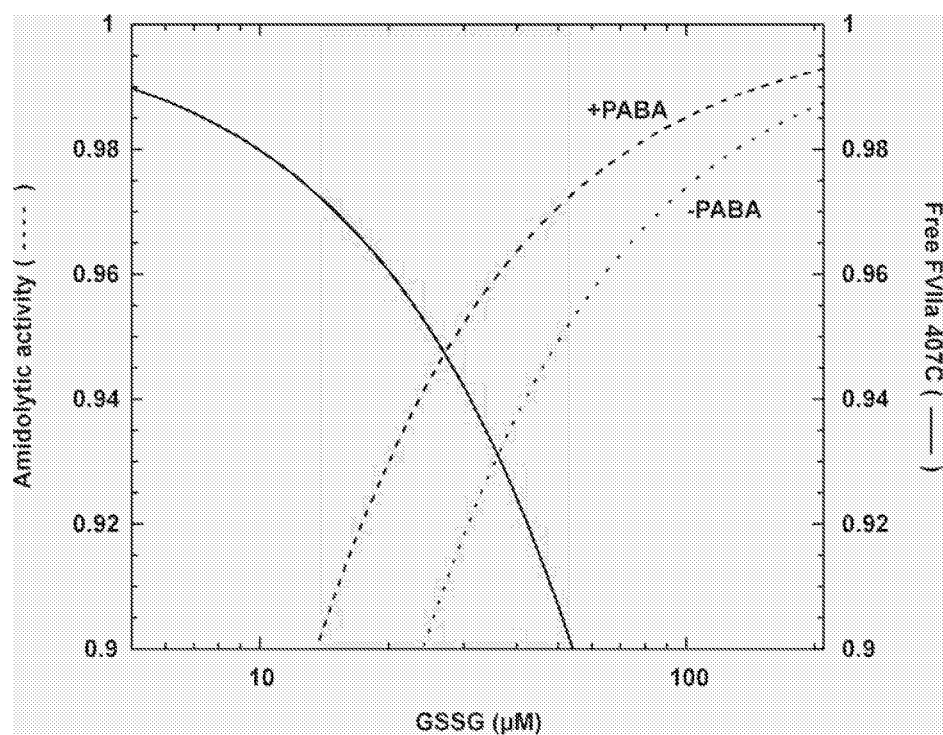
FIG. 4: Residual amidolytic activity (stippled lines) and fraction of FVIIa 407C with a free Cys407 thiol group (solid line) at equilibrium in a redox buffer consisting of 0.5 mM GSH, varying concentrations of GSSG, and either no (−PABA) or 25 mM p-aminobenzamidine (+PABA). Curves were drawn using Eq. 2 and 4, $K_{ox}$ values of 93 (−PABA) and 166 mM (+PABA), respectively, and a $K_{scox}$ value of 1.02. The shaded area indicates the concentration range of GSSG resulting in >90% residual activity and >90% free 407C thiol.

The optimal redox conditions can be determined by performing a redox titration of the protein as known to the person skilled in the art and as demonstrated in FIGS. 2, 3, and 4; see also Gilbert (1995).

In one embodiment, the redox buffer is a redox pair of reduced and oxidized glutathione, and the concentration of the reduced glutathione is in the range of 0-100 mM, and the ratio between reduced glutathione and oxidized glutathione is in the range of 2-200.

In another embodiment, the engineered protein is a protein with labile disulfide bonds. As used herein the phrase "protein with labile disulfide bonds" means a protein exhibiting a progressive loss of biological activity (such as e.g. 50% relative to the original biological activity within 2 hrs) when incubated at around 25 degree under non-denaturing conditions at approx. neutral pH in the presence of 5 mM dithiothreitol (DTT).

In another embodiment, the redox buffer is a redox pair of reduced and oxidized glutathione, and the concentration of the reduced glutathione is in the range of 0-100 mM, e.g. 0.01-50 mM, and the concentration of the oxidized glutathione is in the range of 0-5 mM, e.g. 0.001-5 mM. For Factor VII polypeptides, the concentration of the reduced glutathione is preferably in the range of 0-5 mM, e.g. 0.01-2 mM, and the concentration of the oxidized glutathione is in the range of 0.001-2 mM, e.g. 0.001-0.200 mM.

Since glutathione and other low molecular-weight thiols are generally poor reductants/-oxidants in terms of reaction kinetics, a thiol/disulfide redox catalyst is most preferably included in the mixture in conjunction with the redox buffer in order to enhance the rate of the reaction.

Suitable thiol/disulfide redox catalysts to be included in the mixture include dithiol-type and monothiol-type glutaredoxins. Glutaredoxins and their functions are generally described in Fernandes et al. (2004). Useful examples of glutaredoxins are those selected from Grx1, Grx2 or Grx3 from *Escherichia coli* (Holmgren et al., 1995), Grx1p, Grx2p, Grx3p, Grx4p, and Grx5p from *Saccharomyces cerevisiae* (Luikenhuis et al. 1998; Rodriguez-Manzaneque et al., 1999; Grant, 2001), Grx1 and Grx2 from *Homo sapiens* (Padilla et al. 1995; Lundberg et al., 2001), and variants hereof. Variants include, but are not restricted to, dithiol-type glutaredoxins in which the C-terminal cysteine in the CXXC motif has been replaced by another amino acid, typically serine or alanine (see Yang et al., 1998).

The redox catalyst (in particular a glutaredoxin) is preferably used in a concentration of 0.001-20 μM.

It is preferred that the mixture does not comprise a protein disulfide isomerase (PDI).

The redox buffer may further comprise other components such as salts, pH buffers, etc., and the method of the invention may be conducted at any temperature which is suitable for the protein in question, e.g. a temperature in the range of from −5° C. to 50° C., such as in the range of from 0° C. to 25° C., of course dependent on the stability of the protein under the given conditions.

It is to be understood that this method is performed under native conditions meaning under conditions without denaturants, wherein the protein retain its native active conformation.

(B) Triarylphosphine Reducing Agent

As mentioned above, the present invention also provides a method for selective reduction of an engineered protein in its active conformation comprising at least one non-native cysteine, e.g. a coagulation factor or a protein of the trypsin-family of serine proteases. The protein in question comprises one or more cysteine moieties conjugated through a disulfide bridge to a low-molecular weight thiol (RS-Cys), said moiety/moieties not being involved in intramolecular S—S bridges (Cys-S—-S-Cys) when the protein is in its active form, the method comprising the step of allowing the low-molecular weight thiol-conjugated protein to react with a triarylphosphine reducing agent under non-denaturing conditions.

The term "triarylphosphine reducing agent" is intended to mean a triarylphosphine optionally substituted with one or more substituents.

The aryl groups of the triarylphosphine reducing agent are preferably selected from phenyl, naphthyl, 1,2,3,4-tetrahydronaphthyl, anthracyl, phenanthracyl, pyrenyl, benzopyrenyl, fluorenyl and xanthenyl, in particular phenyl, and in currently selected embodiments, the aryl groups are preferably identical. In the currently most interesting embodiment, all three aryl groups are phenyl. Examples of substituents, which may be present in the aryl groups, in particular phenyl groups, are typically those selected from sulfonic acid, carboxylic acid, $C_{1-6}$-alkyl, $C_{1-6}$-alkoxy, and $C_{1-6}$-alkoxy-$C_{1-6}$-alkyl, or $C_{3-6}$-alkylene (representing a ring with two neighboring aryl carbon atoms) or $C_{2-6}$-alkyleneoxy (representing a ring with two neighboring aryl carbon atoms) or $C_{1-4}$-alkylene-oxy-$C_{1-4}$-alkylene (representing a ring with two neighboring aryl carbon atoms).

In the currently most interesting embodiments, at least one aryl (e.g. phenyl) has at least one substituent selected from sulfonic acid and carboxylic acid, in particular sulfonic acid; such substituent preferably being arranged in the meta position relative to the bond to the phosphor atom.

Preferably, all three aryl groups have a sulfonic acid substituent, e.g. all three aryl groups have a sulfonic acid substituent and at least one further substituent, in particular at least a substituent in the para-position relative to the bond to the phosphor atom, in particular an oxygen substituent in this para-position.

It is currently believed that the aryl groups of preferred reducing agents do not have any substituents in the ortho-position relative to the bond to the phosphor atom.

The term "$C_{1-6}$-alkyl" is intended to encompass linear or branched saturated hydrocarbon residues which have 1-6 carbon atoms. Particular examples are methyl, ethyl, n-propyl, isopropyl, n-butyl, isobutyl, sec-butyl, tert-butyl, n-pentyl, isopentyl, n-hexyl, etc. Similarly, the term "$C_{1-4}$-alkyl" encompasses linear or branched saturated hydrocarbon residues which have 1-4 carbon atoms. The terms "$C_{1-6}$-alkylene", "$C_{2-6}$-alkylene", etc. represent the biradicals corresponding to "$C_{1-6}$-alkyl", "$C_{2-6}$-alkyl", respectively.

Suitable triarylphosphine reducing agents are those having a useful balance between reduction potential and steric hinderance. The chemical nature of the triarylphosphine reducing agent is dictated by its ability to cleave the protein-low-molecular weight thiol mixed disulfide (RS-Cys) while preserving the integrity of the native disulfide bonds in the protein. Currently very interesting compounds are triarylphosphine trisulfonic acids, such as triphenylphosphine-3,3',3"-trisulfonic acid and analogues hereof. Illustrative examples hereof are triarylphosphine reducing agents selected from triphenylphosphine-3,3',3"-trisulfonic acid and analogues thereof, e.g. one of those selected from the compounds 9-11 below:

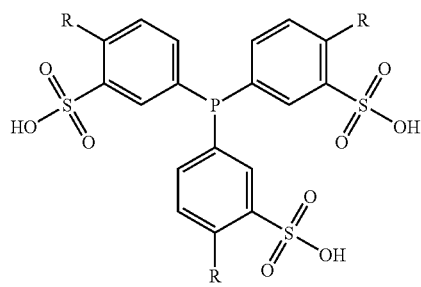

R = H, Me, Et, Pr, 2-Pr, Bu,
MeO, EtO, PrO, 2-PrO, BuO.

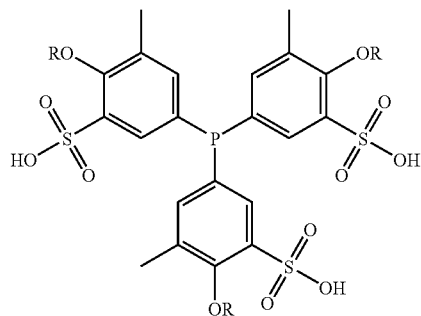

R = Me, Et, Pr, 2-Pr, Bu.

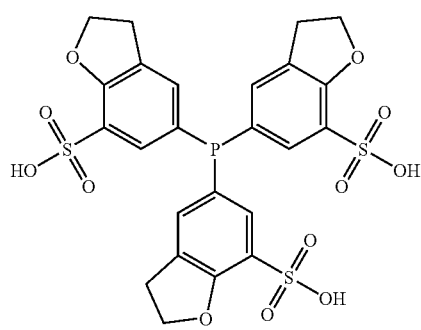

The triarylphosphine reducing agent is preferably used in a concentration of 0.001-100 mM, such as 0.01-50 mM or 0.1-25 mM.

In one interesting embodiment, the triarylphosphine reducing agent is immobilized to a solid support. This will facilitate the easy separation of the reducing agent from the protein. In general, triarylphosphine reducing agent, such as compounds 9-11, may be immobilized by means known to the person skilled in the art, e.g. by introducing a linker group in one of the aryl groups. The triarylphosphine reagent 12 is an example of a linkable variant of 1.

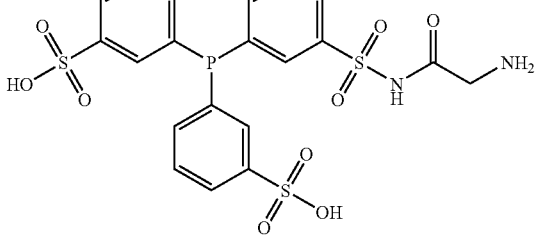

The reaction is typically conducted at a temperature in the range of 0-40° C., such as at ambient temperature, for a period of from 5 seconds to several days, as the case may be. The reaction may be followed by HPLC in order to confirm the conversion. The solvent is preferably an aqueous buffer, optionally including co-solvents such as DMSO or DMF. The solvent may also comprise salts, e.g. calcium salts.

In one variant, the triarylphosphine reducing agent is used in combination with an inhibitor for the protein, e.g. an active site $S_1$ pocket inhibitor, see further below.

The Protein

The selective reduction strategy using a redox buffer as described above is believed to be generally applicable for engineered proteins comprising at least one non-native cysteine, in particular such proteins having engineered cysteines not being involved in intramolecular S—S bridges (Cys-S—S-Cys) when the protein is in its active form, and therefore potentially being in low-molecular weight thiol-conjugated (RS-Cys) form.

The term "low-molecular weight thiol-conjugated (RS-Cys) form" and similar terms are intended to mean that a thiol group of a cysteine of the protein in question is conjugated with a compound having a thiol group, wherein said compound has a molecular weight of less than 500 Da. Examples of such compounds are glutathione, gamma-glutamylcysteine, cysteinylglycine, cysteine, N-acetylcysteine, cysteamine, etc.

The term "active form" refers to the form (or forms) of the protein wherein it is capable of performing a desirable action, e.g. as a catalyst (enzyme), zymogen, or as a co-factor, etc. The "active form" is sometimes referred to as the "correctly folded form".

In one interesting embodiment, a substantial portion of the protein (i.e. at least 50%) is in its active form when the selective reduction reaction is conducted.

An important class of such proteins (which have been subjected to introduction of a non-native cysteine by "protein engineering") includes coagulation factor polypeptides, in particular those selected from Factor II polypeptides (FII/FIIa), Factor VII polypeptides (FVII/FVIIa), Factor VIII polypeptides (FVIII/FVIIIa), Factor IX polypeptides (FIX/FIXa), Factor X polypeptides (FX/FXa), Factor XI polypeptides (FXI/FXIa), Factor XIII polypeptides (FXIII/FXIIIa), and protein C polypeptides, among which Factor VII polypeptides are particularly interesting.

Another very interesting class of "engineered" proteins includes polypeptides corresponding to proteins of the trypsin-family of serine proteases, in particular those selected from Factor II polypeptides (FII/FIIa), Factor VII polypeptides (FVII/FVIIa), Factor IX polypeptides (FIX/FIXa), Factor X polypeptides (FX/FXa), Factor XI polypeptides (FXI/FXIa), and protein C polypeptides, among which Factor VII polypeptides are particularly interesting.

Another very interesting class of "engineered" proteins includes antibodies.

The term "antibody", as used herein, is intended to refer to immunoglobulin molecules and fragments thereof that have the ability to specifically bind to an antigen.

Examples of binding fragments encompassed within the term "antibody" include (i) a Fab fragment, a monovalent fragment consisting of the VL, VH, CL and CH I domains; (ii) F(ab)$_2$ and F(ab')2 fragments, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Na-ture 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426: and Huston et al. (1988) Proc. Natl. Acad. Sci. USA 85:5879-5883). Such single chain antibodies are also intended to be encompassed within the term "antibody". Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Hol-liger, P., et al. (1993) Proc. Natl. Acad. Sci. USA 90:6444-6448; Poljak, R. J., et al. (1994) Structure 2:1121-1123).

The protein is generally an "engineered" polypeptide which compared to a native protein includes at least one non-native cysteine. Such "engineered" polypeptides are preferably prepared by recombinant techniques as will be apparent for the person skilled in the art; see also WO 02/077218 A1 and WO 01/58935 A2.

As mentioned above, a particularly interesting protein is a Factor VII polypeptide.

As used herein "non-denaturing conditions", means conditions wherein the protein substantially retain an intact conformation, wherein the biological activity is substantially preserved, e.g. 60% or more, or 80% or more, such as 90% or more of the activity is preserved as compared to the activity of the starting product.

As used herein, the terms "Factor VII polypeptide", "FVII polypeptide", and the like, means any protein comprising the amino acid sequence 1-406 of wild-type human Factor VIIa (i.e., a polypeptide having the amino acid sequence disclosed in U.S. Pat. No. 4,784,950), variants thereof as well as Factor VII-related polypeptides, Factor VII derivatives and Factor VII conjugates, wherein at least one amino acid has been substituted by a cysteine. This includes FVII variants, Factor VII-related polypeptides, and Factor VII derivatives exhibiting substantially the same or improved biological activity relative to wild-type human Factor VIIa.

The terms "Factor VII" or "FVII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "Factor VII-related polypeptides" encompasses polypeptides, including variants, in which the Factor VIIa biological activity has been substantially modified, such as reduced or truncated (e.g. Gla-domain less variants), relative to the activity of wild-type Factor VIIa. These polypeptides include, without limitation, Factor VII or Factor VIIa into which specific amino acid sequence alterations have been introduced that modify or disrupt the bioactivity of the polypeptide, at least one such modification being an introduced cysteine.

The term "Factor VII derivative" as used herein, is intended to designate a FVII polypeptide exhibiting substantially the same or improved biological activity relative to wild-type Factor VII, in which one or more of the amino acids of the parent peptide have been genetically and/or chemically and/or enzymatically modified, e.g. by alkylation, glycosylation, deglycosylation, PEGylation, acylation, ester formation or amide formation or the like. This includes but is not limited to PEGylated Factor VIIa, cysteine-PEGylated human Factor VIIa and variants thereof.

The term "PEGylated Factor VIIa" (and the like) means a Factor VII polypeptide conjugated with a PEG molecule. It is to be understood, that the PEG molecule may be attached to any part of the Factor VII polypeptide including any amino acid residue or carbohydrate moiety of the Factor VII polypeptide. The term "cysteine-PEGylated Factor VII" means Factor VII polypeptide having a PEG molecule conjugated to a sulfhydryl group of a non-native cysteine of the Factor VII polypeptide.

Non-limiting examples of Factor VII derivatives includes GlycoPegylated FVII derivatives as disclosed in WO 03/31464 and US patent applications US 20040043446, US 20040063911, US 20040142856, US 20040137557, and US 20040132640 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human Factor VIIa or ii) to FVII polypeptides with substantially the same or increased TF binding activity compared to recombinant wild type human Factor VIIa or iii) to FVII polypeptides with substantially the same or increased half life in blood plasma compared to recombinant wild type human Factor VIIa. The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

Non-limiting examples of Factor VII variants having substantially the same or increased proteolytic activity compared to recombinant wild type human Factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, PCT/DK02/00635 (corresponding to WO 03/027147), Danish patent application PA 2002 01423 (corresponding to WO 04/029090), Danish patent application PA 2001 01627 (corresponding to WO 03/027147); WO 02/38162 (Scripps Research Institute); and FVIIa variants with enhanced activity as disclosed in IP 2001061479 (Chemo-Sero-Therapeutic Res Inst.).

Specific examples of interesting "engineered" Factors VII polypeptides are those disclosed in WO 02/077218 A1 (Novo Nordisk A/S) and WO 01/58935 A2 (Maxygen ApS) pages 21-24.

Examples of positions, wherein cysteine residues may be introduced include, but is not limited to, positions at or in the vicinity of the proteolytic degradation sites. Thus, in an interesting embodiment of the invention the cysteine residue(s) to be introduced, preferably by substitution, is selected from the group consisting of I30C, K32C, D33C, A34C, T37C, K38C, W41C, Y44C, S45C, D46C, L141C, E142C, K143C, R144C, L288C, D289C, R290C, G291C, A292C, S314C, R315C, $K_{316}$C, V317C, L390C, M391C, R392C, S393C, E394C, P395C, R396C, P397C, G398C, V399C, L401C, R402C, A403C, P404C and combinations thereof, in particular selected from the group consisting of K32C, Y44C, K143C, R290C, R315C, $K_{341}$C, R392C, R396C, R402C and combinations thereof. In a further interesting embodiment of the invention the cysteine residue(s) is/are introduced into a position that in wild-type FVII is occupied by a threonine or serine residue having at least 25% of its side chain exposed to the surface. For instance, in the Factor VII polypeptide a cysteine residue is introduced, preferably by substitution, into at least one position selected from the group consisting of S12, S23, S43, S45, S52, S53, S60, S67, T83, S103, T106, T108, S111, S19, S126, T128, T130, S147, T185, S214, S222, S232, T233, T238, T239, T255, T267, T293, T307, S320, T324, S333, S336, T370 and S393. Even more preferable, the cysteine residue is introduced into at least one position of FVII containing an S residue, the position being selected from the group consisting of S12, S23, S43, S45, S52, S53, S60, S67, S103, S111, S119, S126, S147, S214, S222, S232, S320, S333, S336 and S393. In a further embodiment the cysteine residue(s) is/are introduced into a position that in wild-type FVII is occupied by a threonine or serine residue having at least 50% of its side chain exposed to the surface. For instance, in the FVII polypeptide a cysteine residue is introduced, preferably by substitution, into at least one position selected from the group consisting of S23, S43, S52, S53, S60, S67, T106, T108, S111, S119, S147, S214, T238, T267 and T293, even more preferable, a position selected from the group consisting of S23, S43, S52, S53, S60, S67, S111, S119, S147 and S214. In a still further embodiment a cysteine residue is introduced into at least one position selected from any of the above-mentioned positions, which is not located in an active site region. Preferably, the position is one occupied by a T or an S residue. As an example, the Factor VII polypeptide comprises a cysteine residue introduced into at least one position selected from the group consisting of S12, S23, S43, S45, S52, S53, S60, S67, T83, S103, T106, T108, S111, S119, S126, T128, T130, S147, T185, S214, S222, T255, T267, T307, S320, S333, S336, T370 and S393 (having more than 25% of its side chain exposed to the surface), in particular selected from the group consisting of S12, S23, S43, S45, S52, S53, S60, S67, S103, S111, S119, S126, S147, S214, S222, S320, S333, S336 and S393 (occupied by S residue), and, more preferable, from the group consisting of S23, S43, S52, S53, S60, S67, T106, T108, S111, S19, S147, S214 and T267 (having more than 50% of its side chain exposed to the surface), in particular from the group consisting of S23, S43, S52, S53, S60, S67, S111, S119, S147 and S214 (occupied by an S residue). In an even further embodiment a cysteine residue is introduced into at least one position selected from any of the above lists, which is not located in a tissue factor binding site region. Preferably, the position is one occupied by a T or an S residue. As an example, the Factor VII polypeptide comprises a cysteine residue introduced into at least one position selected from the group consisting of S12, S23, S45, S52, S53, S67, T83, S103, T106, T108, S111, S119, S126, T128, T130, S147, T185, S214, S222, T232, T233, T238, T239, T255, T267, T293, S320, T324, S333, S336, T370 and S393 (having more than 25% of its side chain exposed to the surface), in particular selected from the group consisting of S12, S23, S45, S52, S53, S67, S103, S111, S119, S126, S147, S214, S222, T232, S320, S333, S336 and S393 (occupied by S residue), and, more preferable, from the group consisting of S23, S52, S53, S67, T106, T108, S111, S19, S147, S214, T238, T267 and T293 (having more than 50% of its side chain exposed to the surface), in particular from the group consisting of S23, S52, S53, S67, S111, S119, S147 and S214 (occupied by an S residue). In a still further embodiment a cysteine residue is introduced into at least one position selected from any of the above lists, which is neither located in a tissue factor binding site region nor in an active site region. Preferably, the position is one occupied by a T or an S residue. As an example, the Factor VII polypeptide comprises a cysteine residue introduced into at least one position selected from the group consisting of S12, S23, S45, S52, S53, S67, T83, S103, T106, T108, S111, S19, S126, T128, T130, S147, T185, S214, S222, T255, T267, S320, S333, S336, T370 and S393 (having more than 25% of its side chain exposed to the surface), in particular selected from the group consisting of S12, S23, S45, S52, S53, S67, S103, S111, S19, S126, S147, S214, S222, S320, S333, S336 and S393 (occupied by S residue), and, more preferable, from the group consisting of S23, S52, S53, S67, T106, T108, S111, S19, S147, S214 and T267 (having more than 50% of its side chain exposed to the surface), in particular from the group consisting of S23, S52, S53, S67, S111, S19, S147 and S214 (occupied by an S residue).

Other useful examples of Factor VII polypeptide include those where an amino acid at a position selected from 247-260, 393-405 or 406, in particular R396, Q250 or P406, or K157, V158, M298, L305, D334, S336, K337 or F374 has been substituted with a cysteine, or where a cysteine has been introduced in the terminal, e.g. Factor VIIa 407C.

Protein Inhibitor

In one interesting embodiment, the mixture further comprises an inhibitor of the protein. By including an inhibitor in the mixture, it is believed that the conformation of the protein is somewhat stabilized whereby the intramolecular disulfide bonds have a lower tendency to become reduced by the redox buffer. Preferably, the inhibitor of the protein is an active-site inhibitor.

In the case of the protein being a Factor VII polypeptide, the presence of an active-site inhibitor extending into the $S_1$ binding pocket might be required during the selective reduction reaction to protect internal disulfide bonds in the active-site region from reduction. Inhibitors useful for this purpose include benzamidines, such as 4-aminobenzamidine, arginines, and other more potent analogues, see, e.g., those disclosed in WO 05/016365 A3 and those disclosed by Aventis in EP 1 162 194 A1, cf. in particular those defined in claims 1-6 and in sections [0009]-[0052], and in EP 1 270 551 A1, cf. in particular claims 1 and 2 and sections [0010]-[0032].

Conjugation

One important purpose of the selective reduction methods described above is to liberate a cysteine group which can be used for attachment (conjugation) of a chemical group, e.g. a non-polypeptide moiety.

Hence, in one important embodiment, the method further comprises the simultaneous and/or subsequent step of conjugating at least one of the selectively reduced cysteine (HS-Cys) moiety/moieties with a chemical group.

It should be understood that the conjugation of the at least one selectively reduced cysteine moieties with a chemical group may be conducted simultaneously, i.e. by addition of one or more reagents leading to the conjugation to the mixture comprising the redox buffer, or in a subsequent step, e.g. after purification and/or isolation of the selectively reduced protein.

In one embodiment, the chemical group is a protractor group, i.e. a group which upon conjugation to the protein (e.g. Factor VII polypeptide) increases the circulation half-life of said protein or polypeptide, when compared to the un-modified protein or polypeptide. The specific principle behind the protractive effect may be caused by increased size, shielding of peptide sequences that can be recognized by peptidases or antibodies, or masking of glycanes in such way that they are not recognized by glycan specific receptors present in e.g. the liver or on macrophages, preventing or decreasing clearance. The protractive effect of the protractor group can e.g. also be caused by binding to blood components such as albumin, or unspecific adhesion to vascular tissue. The conjugated glycoprotein should substantially preserve its biological activity.

In one embodiment of the invention the protractor group is selected from the group consisting of:

(a) A low molecular organic charged radical (15-1,000 Da), which may contain one or more carboxylic acids, amines sulfonic acids, phosphonic acids, or combination thereof.
(b) A low molecular (15-1,000 Da) neutral hydrophilic molecule, such as cyclodextrin, or a polyethylene chain which may optionally branched.
(c) A low molecular (15-1,000 Da) hydrophobic molecule such as a fatty acid or cholic acid or derivatives thereof.
(d) Polyethyleneglycol with an average molecular weight of 2,000-60,000 Da.
(e) A well defined precision polymer such as a dendrimer with an exact molecular mass ranging from 700 to 20,000 Da, or more preferable between 700-10,000 Da.
(f) A substantially non-immunogenic polypeptide such as albumin or an antibody or part of an antibody optionally containing an Fc-domain.
(g) A high molecular weight organic polymer such as dextran.

In another embodiment of the invention the protractor group is selected from the group consisting of dendrimers, polyalkylene oxide (PAO), including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, and dextran, including carboxymethyl-dextran. In one particularly interesting embodiment of the invention, the protractor group is a PEG group.

The term "branched polymer", or interchangebly "dendritic polymer", "dendrimer" or "dendritic structure" means an organic polymer assembled from a selection of monomer building blocks of which, some contains branches.

In one embodiment of the invention the protractor group is a selected from the group consisting of serum protein binding-ligands, such as compounds which bind to albumin, like fatty acids, $C_5$-$C_{24}$ fatty acid, aliphatic diacid (e.g. $C_5$-$C_{24}$). Other examples of protractor groups includes small organic molecules containing moieties that under physiological conditions alters charge properties, such as carboxylic acids or amines, or neutral substituents that prevent glycan specific recognition such as smaller alkyl substituents (e.g., $C_1$-$C_5$ alkyl). In one embodiment of the invention the protractor group is albumin.

In one embodiment, the chemical group is a non-polypeptide.

In one interesting embodiment, the chemical group is a polyethyleneglycol (PEG), in particular one having an average molecular weight of in the range of 500-100,000, such as 1,000-75,000, or 2,000-60,000.

Conjugation can be conducted as disclosed in WO 02/077218 A1 and WO 01/58935 A2.

Particularly interesting is the use of PEG as a chemical group for conjugation with the protein. The term "polyethylene glycol" or "PEG" means a polyethylene glycol compound or a derivative thereof, with or without coupling agents, coupling or activating moeities (e.g., with thiol, triflate, tresylate, azirdine, oxirane, pyridyldithio, vinyl sulfone, haloacetate, or preferably with a maleimide moiety). Compounds such as maleimido monomethoxy PEG are exemplary of activated PEG compounds of the invention.

PEG is a suitable polymer molecule, since it has only few reactive groups capable of cross-linking compared to polysaccharides such as dextran. In particular, monofunctional PEG, e.g. methoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule are provided in activated form, i.e. with reactive functional groups. Suitable activated polymer molecules are commercially available, e.g. from Shearwater Corp., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Corp. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the polypeptide (examples of which are given further above), as well as the functional groups of the polymer (e.g. being amine, hydroxyl, carboxyl, aldehyde, sulfydryl, succinimidyl, maleimide, vinysulfone or haloacetate). The PEGylation may be directed towards conjugation to all available attachment groups on the polypeptide (i.e. such attachment groups that are exposed at the surface of the polypeptide) or may be directed towards one or more specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form of such molecules (e.g. whether they are linear or branched), and where in the polypeptide such molecules are attached. The molecular weight of the polymer to be used will be chosen taking into consideration the desired effect to be achieved. For instance, if the primary purpose of the conjugation is to achieve a conjugate having a high molecular weight and larger size (e.g. to reduce renal clearance), one may choose to conjugate either one or a few high molecular weight polymer molecules or a number of polymer molecules with a smaller molecular weight to obtain the desired effect.

It has further been found that advantageous results are obtained when the apparent size (also referred to as the "apparent molecular weight" or "apparent mass") of at least a major portion of the conjugate of the invention is at least about 50 kDa, such as at least about 55 kDa, such as at least about 60 kDa, e.g. at least about 66 kDa. This is believed to be due to the fact that renal clearance is substantially eliminated for conjugates having a sufficiently large apparent size. In the present context, the "apparent size" of a protein conjugate or Factor VII polypeptide is determined by the SDS-PAGE method.

Furthermore, it has been reported that excessive polymer conjugation can lead to a loss of activity of the protein (e.g. Factor VII polypeptide) to which the chemical group (e.g. a non-polypeptide moiety) is conjugated (see further below). This problem can be eliminated, e.g., by removal of attachment groups located at the functional site or by reversible blocking the functional site prior to conjugation so that the functional site of the protein is blocked during conjugation. Specifically, the conjugation between the protein and the chemical group (e.g. non-polypeptide moiety) may be conducted under conditions where the functional site of the protein is blocked by a helper molecule e.g. tissue factor capable of binding to the functional site of the protein or a serine protease inhibitor. Preferably, the helper molecule is one, which specifically recognizes a functional site of the protein, such as a receptor, in particular tissue factor, either full length or a suitably truncated form of tissue factor or two molecules, one being tissue factor the other one being a peptide or peptide inhibitor binding to and thus protecting the area around the catalytic triad (preferably defined as amino acid residues within 10 Å of any atom in the catalytic triad).

Alternatively, the helper molecule may be an antibody, in particular a monoclonal antibody recognizing the protein (e.g. Factor VII polypeptide). In particular, the helper molecule may be a neutralizing monoclonal antibody.

The protein is preferably to interact with the helper molecule before effecting conjugation. (Often it is even advantageous to use the same helper molecule (e.g. an inhibitor) as the one used in the steps where mixed disulfides are reduced.) This ensures that the functional site of the protein (e.g. Factor VII polypeptide) is shielded or protected and consequently unavailable for derivatization by the chemical group (e.g. non-polypeptide moiety) such, as a polymer.

Following its elution from the helper molecule, the conjugate of the chemical group and the protein can be recovered with at least a partially preserved functional site.

Preferred Embodiments

In one currently preferred embodiment, the invention relates to a method for selective reduction of a Factor VII polypeptide in its active conformation, said Factor VII polypeptide comprising one or more cysteine moieties conjugated through a disulfide bridge to a low-molecular weight thiol (RS-Cys), said moiety/moieties not being involved in intramolecular S—S bridges (Cys-S—S-Cys) when the Factor VII polypeptide is in its active form, the method comprising the step of allowing the low-molecular weight thiol-conjugated FVII polypeptide to react with a mixture comprising reduced and oxidized glutathione and a glutaredoxin, and the simultaneous and/or subsequent step of conjugating at least one of the selectively reduced cysteine (HS-Cys) moieties with a chemical group each step under non-denaturing conditions.

In another currently preferred embodiment, the invention relates to a method for selective reduction of a Factor VII polypeptide in its active conformation, said Factor VII polypeptide comprising one or more cysteine moieties conjugated through a disulfide bridge to a low-molecular weight thiol (RS-Cys), said moiety/moieties not being involved in intramolecular S—S bridges (Cys-S—S-Cys) when the Factor VII polypeptide is in its active form, the method comprising the step of allowing the low-molecular weight thiol-conjugated Factor VII polypeptide to react with a mixture comprising a triarylphosphine-3,3',3"-trisulfonic acid compound and an active site $S_1$ pocket inhibitor, and the simultaneous and/or subsequent step of conjugating at least one of the selectively reduced cysteine (HS-Cys) moieties with a chemical group each step under non-denaturing conditions.

EXPERIMENTALS

Materials and Methods

Materials—DL-dithiothreitol (DTT) was purchased from Sigma. Reduced and oxidized glutathione (GSH and GSSG, respectively), cysteine (Cys), DL-homocysteine (hCy), cysteinylglycine (CG), and γ-glutamylcysteine (γ-GC) were purchased from Sigma. Cysteamine (Cya) and 7-fluorobenzofurazan-4-sulfonic acid ammonium salt (SBD-f) were obtained from Fluka. Tris(2-carboxyethyl)phosphine (TCEP) was purchased from Calbiochem (Merck KGaA, Darmstadt, Germany). Iodoacetamide was purchased from Sigma. Chromogenic S-2288 substrate was obtained from Chromogenix (Milano, Italy). PEG5k-maleimide (2E2M0H01), PEG20k-maleimide (2E2M0P01), PEG40k-maleimide (2D3Y0T01), and maleimide-PEG3.4 k-maleimide (2E2E0F02) were purchased from Nektar Therapeutics (Huntsville, Ala.). d-Phe-Phe-Arg-chloromethyl ketone was purchased from Bachem. Triphenylphosphine-3,3',3" trisulfonic acid was obtained from Aldrich. Human plasma-derived FX and FXa were obtained from Enzyme Research Laboratories Inc. (South Bend, Ind.). Soluble tissue factor 1-219 (sTF) was prepared according to published procedures (Freskgard et al., 1996). Expression and purification of recombinant FVIIa was performed as described previously (Thim et al., 1988; Persson and Nielsen, 1996). All other chemicals were of analytical grade or better.

Concentration determination—The concentration of GSSG in stock solutions was determined from its absorption at 248 nm using an extinction coefficient of 381 $M^{-1}cm^{-1}$ (Chau and Nelson, 1991). The concentration of GSH, DTT, and other low-molecular weight thiols were determined using Ellman's reagent (5,5'-dithiobis(2-nitrobenzoic acid)) with 14150 $M^{-1}cm^{-1}$ as the molar extinction coefficient of 2-nitro-5-thiobenzoic acid at 412 nm (Riddles et al., 1979).

Quantification of GSSG by HPLC—Quantification of GSSG was performed essentially as described elsewhere (Takahashi and Creighton, 1996). Briefly, 50 μl acid quenched sample were loaded onto a $C_{18}$ reversed-phase column (Luna C18(2) 100 Å, 3 μm particle size, 4.6×50 mm; Phenomenex Inc., Torrance, Calif.) maintained at 30° C. Following 5 min isocratic run at 100% eluent A (0.1% (v/v) trifluoroacetic acid (TFA) in water), GSSG was eluted by a linear gradient from 0-5% eluent B (0.085% (v/v) TFA in acetonitrile) in 5 min at a flow rate of 1 ml/min and detected by absorption at 214 nm. The concentration of GSSG was determined by relating the calculated peak area (Millenium32 v4.0 software, Waters) to a standard curve made with known amounts of GSSG. Linearity was observed in the range from 2-25 nmol GSSG.

Analysis of thiol-modified FVIIa 407C by HPLC—Free and thiol-modified FVIIa 407C species were analyzed by HPLC using a $C_3$ reversed-phase column (Zorbax 300SB-C3, 2.1×150 mm, 5-μm particle size; Agilent Technologies, Denmark) maintained at 45° C. The flow rate was 0.5 ml/min and mobile phases consisted of 0.1% (v/v) TFA in water (eluent A) and 0.085% (v/v) TFA in acetonitrile (eluent B). After injection of 25 μl acid quenched sample, the system was run isocratically at 30% eluent B for 5 min followed by linear gradients from 38-41.5% eluent B over 20 min and 41.5-55% eluent B over 20 min. The eluate was monitored by fluorescence (excitation and emission wavelengths of 280 and 348 nm, respectively).

EXAMPLES

FVIIa contains labile intramolecular disulfide bonds as probed by incubation in the presence of DTT—The presence of labile intramolecular disulfide bonds in FVIIa was determined from the loss of catalytic activity after incubation in the presence of 0, 0.5, 1, or 5 mM of the disulfide reducing agent DTT. The reaction was carried out at room temperature in a reaction buffer (50 mM HEPES, 100 mM NaCl, 10 mM $CaCl_2$, 0.01% Tween80, pH 7.0) containing 300 μM FVIIa, and DTT. At timed intervals, 20 μl reaction was transferred to 160 μl reaction buffer containing 10 mM iodoacetamide to rapidly alkylate free thiols and quench the reaction. Subsequently, residual amidolytic activity was measured in polystyrene microtiter plates (Nunc, Denmark) by addition of 20 μl S-2288 chromogenic substrate to a final concentration 1 mM and the absorbance monitored continuously at 405 nm for 10 min in a SpectraMax™ 340 microplate spectrophotometer equipped with SOFTmax PRO software (v2.2; Molecular Devices Corp., Sunnyvale, Calif.). Amidolytic activity was reported as the slope of the linear progress curves relative to the slope in the absence of DTT at time zero. See Table 3.

TABLE 3

Relative amidolytic activity of FVIIa in the presence of indicated concentrations of DTT. Relative activities were calculated as $100 \times A_t(sample)/A_0(0\ mM\ DTT)$, where $A_t$ denoted the slope of the linear progress curve at time t.

| Time | 0 mM DTT | 0.5 mM DTT | 1 mM DTT | 5 mM DTT |
|---|---|---|---|---|
| 0 min | 100 | 97 | 95 | 75 |
| 10 min | 103 | 91 | 81 | 36 |
| 20 min | 102 | 84 | 69 | 16 |
| 40 min | 106 | 73 | 54 | 6 |
| 60 min | 111 | 65 | 40 | 3 |
| 80 min | 111 | 59 | 30 | 2 |
| 100 min | 119 | 52 | 24 | 2 |
| 120 min | 122 | 45 | 19 | 1 |

Construction of DNA encoding FVII 407C mutant—A DNA construct encoding FVIIa 407C was constructed as described in WO 02/077218 A1

Construction of DNA encoding FVII Q250C mutant—A DNA construct encoding FVIIa Q250C was constructed as described in WO 02/077218 A1

Construction of DNA encoding FVII R396C mutant—A DNA construct encoding FVIIa R396C was constructed as described in WO 02/077218 A1

Expression and purification of FVII 407C—BHK cells were transfected essentially as previously described (Thim et al., 1988; Persson and Nielsen, 1996) to obtain expression of the FVIIa 407C variant. The Factor VII polypeptide was purified as follows:

Conditioned medium was loaded onto a 25-ml column of Q Sepharose Fast Flow (Amersham Biosciences, GE Healthcare) after addition of 5 mM EDTA, 0.1% Triton X-100 and 10 mM Tris, adjustment of pH to 8.0 and adjustment of the conductivity to 10-11 mS/cm by adding water. Elution of the protein was accomplished by a gradient from 10 mM Tris, 50 mM NaCl, 0.1% Triton X-100, pH 8.0 to 10 mM Tris, 50 mM NaCl, 25 mM CaCl$_2$, 0.1% Triton X-100, pH 7.5. The fractions containing FVIIa 407C were pooled, and applied to a 25-ml column containing the monoclonal antibody F1A2 (Novo Nordisk A/S, Bagsvaerd, Denmark) coupled to CNBr-activated Sepharose 4B (Amersham Biosciences, GE Healthcare). The column was equilibrated with 50 mM HEPES, pH 7.5, containing 10 mM CaCl$_2$, 100 mM NaCl and 0.02% Triton X-100. After washing with equilibration buffer and equilibration buffer containing 2 M NaCl, bound material was eluted with equilibration buffer containing 10 mM EDTA instead of CaCl$_2$. Before storage, FVIIa 407C was transferred to a 50 mM HEPES, 100 mM NaCl, 10 mM CaCl$_2$, pH 7.0 buffer by dialysis. The yield of each step was followed by factor VII ELISA measurements and the purified protein was analysed by SDS-PAGE.

Expression and purification of FVII Q250C—BHK cells were transfected essentially as previously described (Thim et al., 1988; Persson and Nielsen, 1996) to obtain expression of the FVIIa Q250C variant. The Factor VII polypeptide was purified as follows:

Conditioned medium was loaded onto a 25-ml column of Q Sepharose Fast Flow (Amersham Biosciences, GE Healthcare) after addition of 5 mM EDTA, 0.1% Triton X-100 and 10 mM Tris, adjustment of pH to 8.0 and adjustment of the conductivity to 10-11 mS/cm by adding water. Elution of the protein was accomplished by a gradient from 10 mM Tris, 50 mM NaCl, 0.1% Triton X-100, pH 8.0 to 10 mM Tris, 50 mM NaCl, 25 mM CaCl$_2$, 0.1% Triton X-100, pH 7.5. The fractions containing FVIIa 407C were pooled, and applied to a 25-ml column containing the monoclonal antibody F1A2 (Novo Nordisk A/S, Bagsvaerd, Denmark) coupled to CNBr-activated Sepharose 4B (Amersham Biosciences, GE Healthcare). The column was equilibrated with 50 mM HEPES, pH 7.5, containing 10 mM CaCl$_2$, 100 mM NaCl and 0.02% Triton X-100. After washing with equilibration buffer and equilibration buffer containing 2 M NaCl, bound material was eluted with equilibration buffer containing 10 mM EDTA instead of CaCl$_2$. Before storage, FVIIa Q250C was transferred to a 50 mM HEPES, 100 mM NaCl, 10 mM CaCl$_2$, pH 7.0 buffer by dialysis. The yield of each step was followed by factor VII ELISA measurements and the purified protein was analysed by SDS-PAGE.

Expression and Purification of FVII R396C—Expression and Purification of FVIIa R396C was Performed as Described in WO 02/077218 A1

Cloning and expression of glutaredoxins—DNA coding sequences for *Escherichia coli* glutaredoxin 2 (Grx2) and *Saccharomyces cerevisiae* glutaredoxin 1 (yGrx1p) were amplified by PCR using Expand High Fidelity PCR system (Roche Diagnostics Corporation, Indianapolis, Ind.) according to manufacturer's recommendations and primer pairs oHOJ98-f/oHOJ398-r and oHOJ11-f/oHOJ11-r, respectively, introducing flanking NdeI and XhoI restriction sites (primer sequences are listed in Table 1).

TABLE 1

DNA oligos used for construction of plasmids pHOJ294, 210, and 286 expressing *E. coli* glutaredoxin 2 (Grx2), *S. cerevisiae* glutaredoxin 1 (yGrx1p), and yGrx1p C30S, respectively. NdeI and XhoI restriction sites are shown in bold face.

| Primer | Plasmid | Target | Sequence (5'→3') |
|---|---|---|---|
| oHOJ11-f | pHOJ210 | yGrx1p | GGGCCGCCCATATGGTATCTCAAGAAACTATC (SEQ ID NO: 1) |
| oHOJ11-r | pHOJ210 | yGrx1p | GCCCGGGCTCGAGATTTGCAAGAATAGGTTCTAAC (SEQ ID NO: 2) |
| oHOJ98-f | pHOJ294 | Grx2 | GCCGCCGGCATATGAAGCTATACATTTACGATCACTGCCC (SEQ ID NO: 3) |
| oHOJ98-r | pHOJ294 | Grx2 | CCGCCGCCCTCGAGAATCGCCATTGATGATAACAAATTGATTTGTG (SEQ ID NO: 4) |
| oHOJ88-f | pHOJ286 | yGrx1p C30S | GTTTAGGGCTGCATGCGAGTATGGACAGTACG (SEQ ID NO: 5) |
| oHOJ88-r | pHOJ286 | yGrx1p C30S | CGTACTGTCCATACTCGCATGCAGCCCTAAAC (SEQ ID NO: 6) |

Genomic template DNA for PCR reactions was prepared from *E. coli* and *S. cerevisiae* according to published procedures (Grimberg et al., 1989; Hoffman and Winston, 1987). The purified PCR products were cut with NdeI and XhoI and then ligated into the corresponding sites of pET-24a(+) (Novagen) to give pHOJ294 and pHOJ210, respectively. Since stop codons were provided by the vector, the two genes were equipped with 3' vector-derived extensions encoding C-terminal LEHHHHHH affinity tags. Plasmid pHOJ286 encoding yGrx1p Cys30→Ser (yGrx1p C30S) was constructed by QuickChange® Site-Directed Mutagenesis using primers oHOJ88-f/oHOJ88-r and pHOJ210 as template according to manufacturer's instructions (Stratagene, La Jolla, Calif.). The correct identity of all cloned sequences was verified by DNA sequencing.

For expression, pHOJ210, 286, and 294 plasmids were introduced into chemical competent BL21(DE3) cells (Stratagene, La Jolla, Calif.). Fresh overnight transformants were inoculated into 500 ml terrific broth ((Sambrook et al., 1989)) and 30 μg/ml kanamycine to an initial OD$_{600}$ of 0.02. Cultures were grown at 37° C. in baffled flasks at 230 rpm to the mid-log phase (OD$_{600}$ 3-4) at which time the temperature was lowered to 25° C. and protein expression induced by 0.1 mM isopropyl-β-D-thiogalactopyranoside (ITPG). After overnight expression, cells were harvested by centrifugation, resuspended in 50 ml lysis buffer (50 mM potassium phosphate, 300 mM NaCl, pH 8.0), and lysed by three freeze-thaw cycles. The cleared lysate was loaded onto a 20-ml Ni-NTA Superflow (Qiagen GmbH, Hilden, Germany) column equilibrated with lysis buffer at a flow rate of 5 ml/min. After washing with lysis buffer, bound protein was eluted with a linear gradient from 0-200 mM imidazole in lysis buffer. Peak fractions were pooled, treated with 20 mM dithiothreitol for 20 min before extensive dialysis against 50 mM Tris-HCl, 2 mM EDTA, pH 8.0. Proteins were stored at −80° C. and judged to be >90% pure by SDS-PAGE. Concentrations were estimated by absorbance at 280 nm using extinction coefficients of 5240 $M^{-1}cm^{-1}$ (yGrx1p and yGrx1p C30S) and 21740 $M^{-1}cm^{-1}$ (Grx2).

Identification of low-molecular weight thiols engaging in mixed disulfides with FVIIa 407C—HPLC detection of fluorescent SBD-derivatized low-molecular weight thiols was performed as described by Oe et al. (1998) with minor modifications. Briefly, disulfide reduction and subsequent derivatization of liberated thiols was performed by incubating 25 µl of 10 µM FVIIa 407C (or wild-type FVIIa) in 160 mM Tris-HCl, 8 mM EDTA, pH 9.6 buffer with 5 µl 14 mM TCEP (in water) and 10 µl 0.3% SBD-f (in water) at 60° C. for 60 min. Subsequently, derivatization was terminated by addition of 2 µl 5 M HCl and samples were placed at 4° C. until further analysis (within 24 hr). HPLC analysis was performed by injecting 25-µl aliquots of the samples onto a reversed-phase C18(2) column (Luna, 100 Å, 3.5 µm particle size, 150×4.6 mm; Phenomenex Inc., Torrance, Calif.) at a flow rate of 1 ml/min. The column temperature was maintained at 30° C. SBD-derivatized thiols were separated by isocratic elution using a mobile phase consisting of 75 mM Na-Citrate, pH 2.90 and 2% methanol and detected by the fluorescence emitted at 516 nm upon excitation at 386 nm. Peak identification was performed by comparison of retention times with those of a series of known low-molecular weight thiol compounds prepared according to the procedure described above for FVIIa 407C. Calibration curves for quantification of GSH, γ-GC, GC, Cys, Hcy, and Cya were obtained by varying the concentration of each thiol from 0.4 to 3.5 µM in the final reaction mixture.

Figure 1:
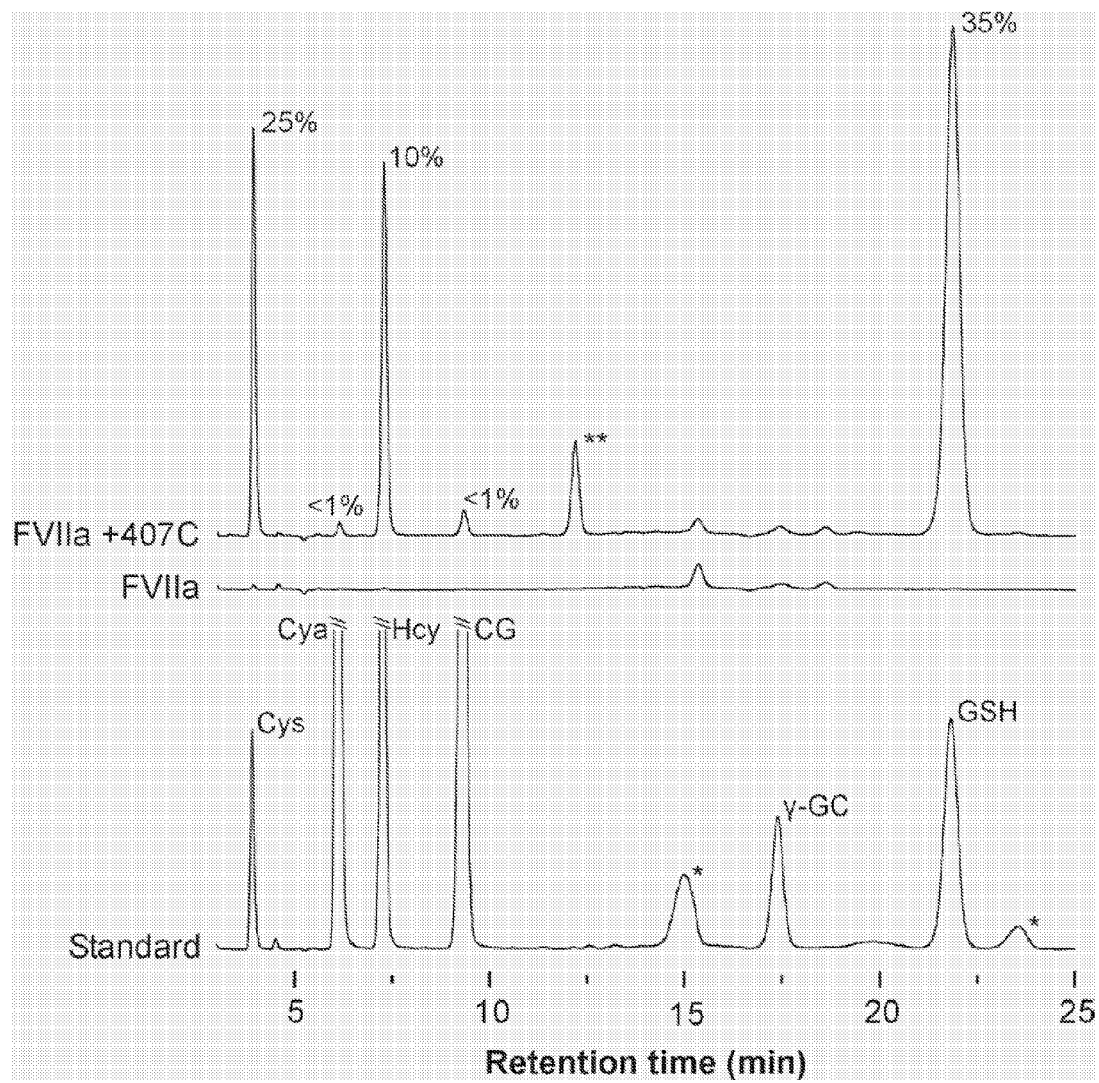
FIG. 1: Identification of low-molecular weight thiols engaged in mixed disulfides with FVIIa 407C. Protein was incubated in the presence of TCEP and SBD-f to liberate and derivatize thiols attached to the engineered Cys407 in the preparation of FVIIa 407C. SBD-derivatized thiols were separated by reversed-phase HPLC and detected by fluorescence (excitation and emission wavelengths of 386 and 516 nm, respectively). HPLC traces of wild-type FVIIa and a series of low-molecular weight thiol compounds (10 pmol of each; denoted standard) are shown for comparison. Peaks marked with an asterisk arise from impurities in commercially available cysteamine. The two asterisks indicate a peak of unknown identity in the HPLC trace of FVIIa 407C. Percentages above each peak indicate the amount of a given thiol species (identified from its retention time) relative to the amount of FVIIa 407C analyzed. Based on retention times, it can be concluded that major thiols conjugated to FVIIa 407C are glutathione, cysteine, and homocysteine. Abbreviations: GSH (glutathione), γ-GC (γ-glutamylcysteine), CG (cysteinylglycine), Cys (cysteine), Hcy (homocysteine) and Cya (cysteamine).

From this analysis, it can be concluded that major low-molecular weight thiols conjugated to FVIIa 407C are glutathione, cysteine, and homocysteine. Results are presented in FIG. 1.

Redox titration of FVIIa—To identify conditions appropriate for selective reduction of FVIIa Cys mutants, the structural stability of FVIIa was assessed in buffers with defined redox potentials obtained by varying concentrations of GSH and GSSG essentially as described elsewhere (Loferer et al., 1995). Since reduction of the two most labile disulfide bonds in FVIIa has been shown to be associated with a loss of amidolytic activity and sTF binding (Higashi et al., 1997), the structural integrity of FVIIa was monitored by its ability to hydrolyse the chromogenic substrate S-2288 in the presence of sTF.

Redox titration of FVIIa (1 µM) was performed in 50 mM HEPES, 100 mM NaCl, 5 mM $CaCl_2$, pH 7.0 buffer (thoroughly purged with nitrogen) containing 50 µM GSSG and varying concentrations of GSH (0-34 mM). In addition, one series of samples contained 25 mM p-aminobenzamidine, an active-site inhibitor of FVIIa occupying the $S_1$ pocket (Sichler et al., 2002; Persson et al., 2004). To reduce the time required to reach equilibrium, reactions were performed in the presence of 1 µM yGrx1p acting as a redox catalyst (Ostergaard et al., 2004). After equilibration of the samples for 3.5 hours at 30° C. under nitrogen atmosphere, residual amidolytic activity was determined as described below. At the same time, an aliquot of the reaction mixture was quenched by an equal volume of 100 mM HCl, and the equilibrium concentration of GSSG determined by HPLC as described in materials and methods.

For measurement of residual amidolytic activity, 20 µl of the equilibrated samples were diluted 20-fold into assay buffer (50 mM HEPES, 100 mM NaCl, 5 mM $CaCl_2$, 0.01% Tween 80, pH 7.4) containing 10 mM iodoacetamide to rapidly alkylate free thiols and prevent subsequent thiol oxidation. The activity assay was carried out in polystyrene microtiter plates (Nunc, Denmark) in a final volume of 200 µl assay buffer containing 80 nM sTF and quenched sample to a final concentration of 10 nM FVIIa. After 15 min pre-incubation at room temperature, 1 mM chromogenic substrate S-2288 was added and the absorbance monitored continuously at 405 nm for 20 min in a SpectraMax™ 340 microplate spectrophotometer equipped with SOFTmax PRO software (v2.2; Molecular Devices Corp., Sunnyvale, Calif.). Amidolytic activity was reported as the slope of the linear progress curves after blank subtraction.

Data were analyzed in terms of the following reaction (Eq. 1), where FVIIa is converted into inactivated FVIIa (denoted FVIIai) by reversible reduction of a single intramolecular disulfide bond:

$$FVIIa+2GSH \Leftrightarrow FVIIai+GSSG \qquad \text{Eq. 1}$$

The apparent equilibrium constant for the reverse reaction ($K_{ox}$) can be estimated from the following relationship (Eq. 2)

$$f=a_{max}/(1+[GSH]^2/([GSSG]K_{ox})) \qquad \text{Eq. 2}$$

where f is the residual amidolytic activity at a given $[GSH]^2/[GSSG]$, and $a_{max}$ is the limiting amidolytic activity at low $[GSH]^2/[GSSG]$.

Fitting the redox titration data to Eq. 2 by non-linear least squares regression using Kaleidagraph software (v3.6, Synergy software) yielded apparent $K_{ox}$'s of 93±6 mM and 166±16 mM in the absence or presence of 25 mM p-aminobenzamidine, respectively (FIG. 2).

Redox titration of FVIIa 407C-glutathione mixed disulfide—The stability of the mixed disulfide between glutathione and Cys407 was measured by incubating 13 µM FVIIa 407C in 50 mM HEPES, 100 mM NaCl, 10 mM $CaCl_2$, pH 7.0 containing 0.5 mM GSH and varying concentrations of GSSG (5-500 µM). In addition, all samples contained 10 µM Grx2 to catalyze the reaction. After 5 hours equilibration at 30° C., a 50-µl aliquot was quenched with 100 mM HCl and the equilibrium concentration of GSSG determined by HPLC as described in materials and methods. To measure the relative amount of deglutathionylated FVIIa 407C, free thiols were labelled with PEG5k by combining 20 µl of each sample with 15 µl 1.6 mM PEG5k-maleimide. Following 18 min incubation at room temperature, N-ethylmaleimide was added to a final concentration of 25 mM to competitively suppress further (unspecific) PEGylation of the protein during subsequent processing. PEG5k-modified FVIIa 407C in each sample was detected and quantified by HPLC as described in material and methods.

Data were analyzed according to the following reaction (Eq. 3), where glutathionylated FVIIa 407C (FVIIa 407C-GSH) reacts with GSH to give free FVIIa 407C and GSSG $$FVIIa\ 407C\text{-}GSH+GSH \Leftrightarrow FVIIa\ 407C+GSSG \qquad \text{Eq. 3}$$

The apparent equilibrium constant for the reverse reaction, denoted $K_{scox}$, can be estimated from the following relationship (Eq. 4)

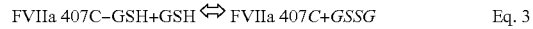
$$A_{407C\text{-}PEG5k}=A_{max}([GSH]/[GSSG])/([GSH]/[GSSG]+K_{scox}) \qquad \text{Eq. 4}$$

where $A_{407C-PEG5k}$ is the peak area of 5k-PEGylated FVIIa 407C at a given [GSH]/[GSSG] ratio, and $A_{max}$ is the limiting peak area at high [GSH]/[GSSG].

A plot of the measured peak areas versus the [GSH]/[GSSG] ratio at equilibrium is shown in FIG. 3. Fitting of Eq. 4 to the data by non-linear least squares regression using Kaleidagraph software (v3.6, Synergy software) gave an apparent $K_{scox}$ of 1.0, very similar to that measured for a range of other glutathionylated proteins (Gilbert, 1995).

Figure 5:
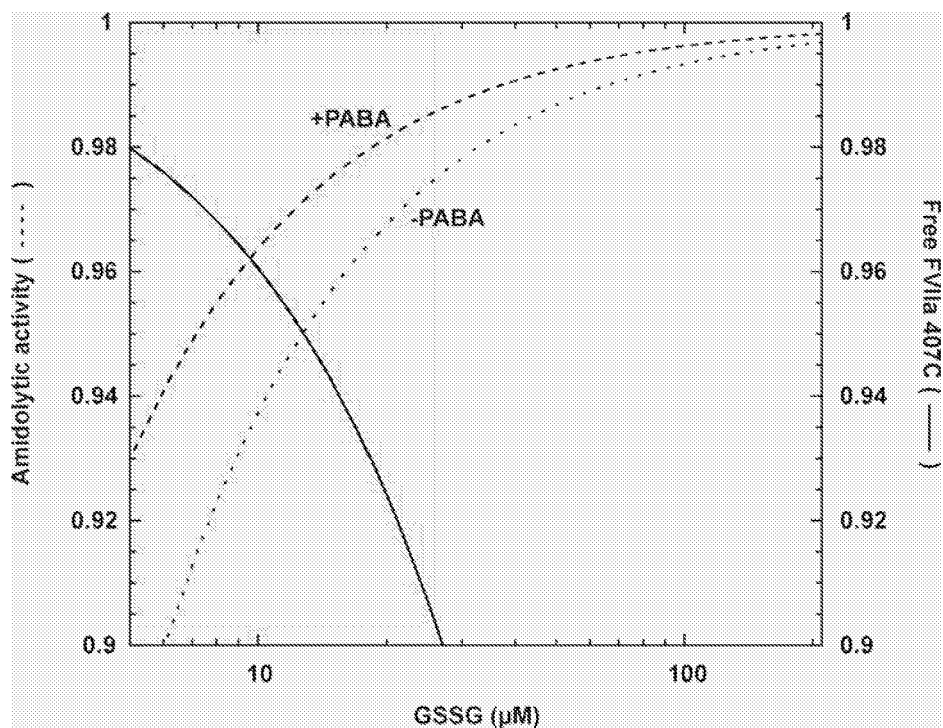
FIG. 5: As FIG. 4 with 0.25 mM GSH instead. The shaded area indicates the concentration range of GSSG resulting in >90% residual activity and >90% free FVIIa 407C thiol.
Figure 6:
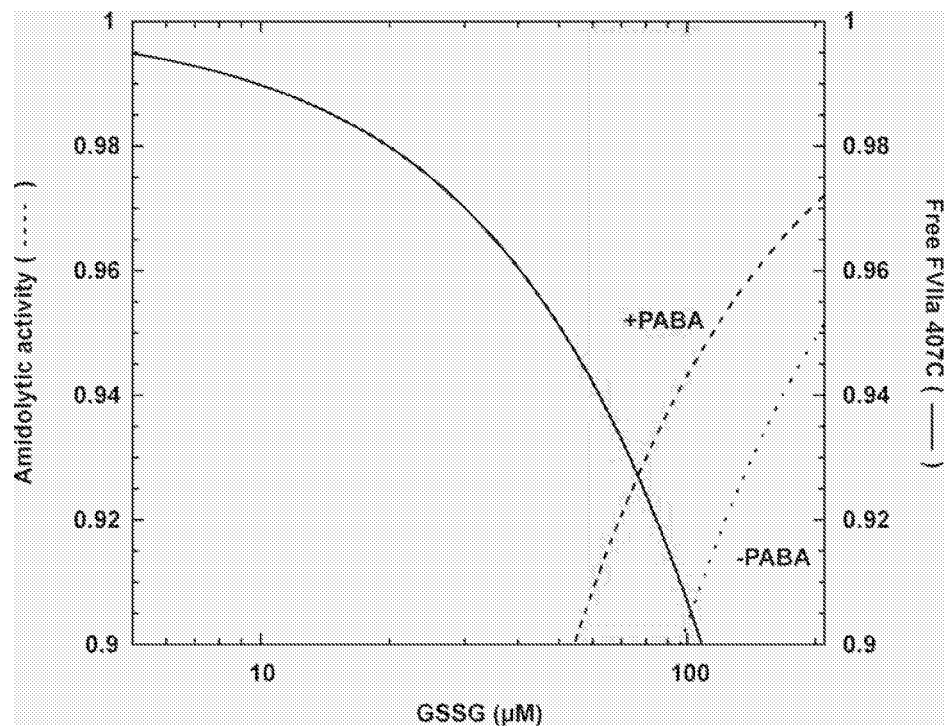
FIG. 6: As FIG. 4 with 1.0 mM GSH instead. The shaded area indicates the concentration range of GSSG resulting in >90% residual activity and >90% free FVIIa 407C thiol.

Identification of optimal reduction conditions—Optimal glutathione redox conditions supporting selective reduction of the FVIIa 407C—mixed disulfides were identified from plots of the following parameters as a function of [GSSG]: (1) the residual amidolytic activity in the presence or absence of p-aminobenzamidine using Eq. 2 and estimated $K_{ox}$ values, and (2) the fraction of selectively reduced protein from Eq. 4 and $K_{scox}$. For practical reasons, the concentration of GSH was set to 0.5 mM. As shown in FIG. 4, a concentration of GSSG between roughly 15 and 60 μM in the presence of 0.5 mM GSH results in >90% residual activity and >90% free Cys407. The optimal [GSSG] working range depends on several parameters, including the concentration of GSH (as exemplified in FIGS. 3-5), the values of $K_{ox}$ and $K_{scox}$ (not shown), and the allowed loss of amidolytic activity during the reduction reaction.

Figure 7:
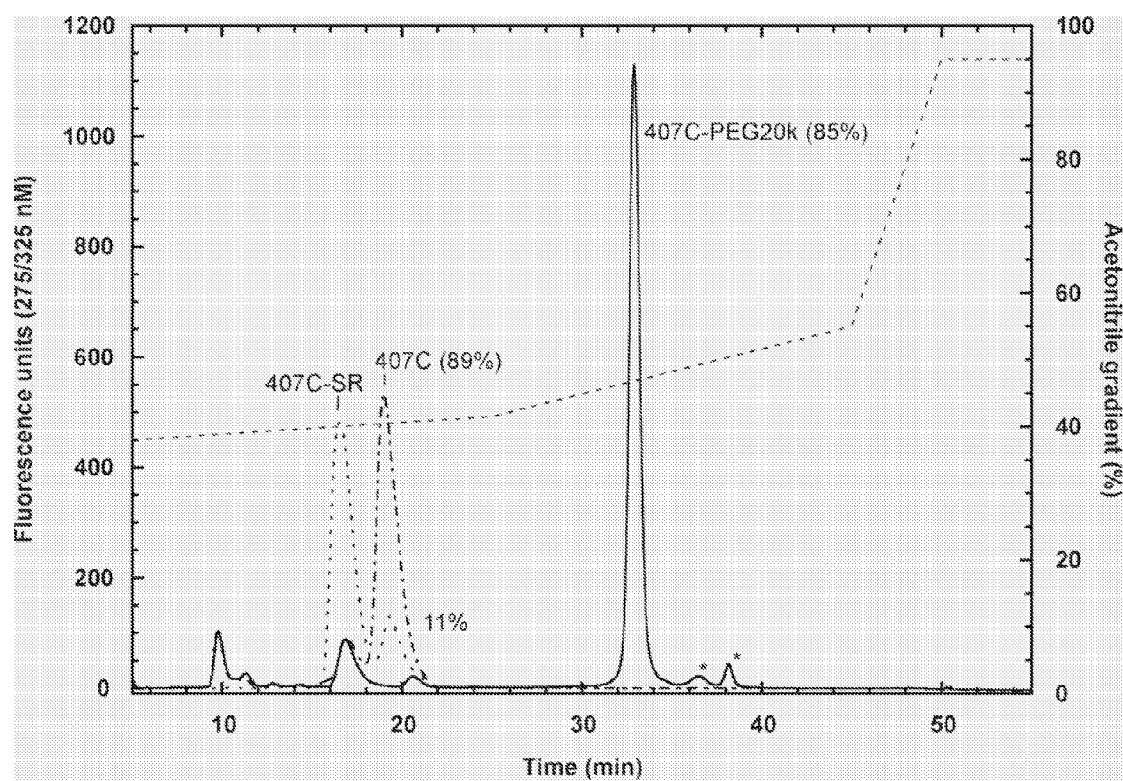
FIG. 7: HPLC analysis of FVIIa 407C before (dotted line) and after selective reduction (dashed-dotted line), and after modification with PEG20k-maleimide (solid line). 407C, 407C-SR, and 407C-PEG20k indicate peaks representing free, low-molecular weight thiol-conjugated, and 20k-PEGylated FVIIa 407C, respectively. Asterisks indicate peaks of unknown identity probably representing hyper-PEGylated species. Peak integration yielded 89% free FVIIa 407C at the end of the reduction step versus 11% in the untreated material. After thiol alkylation, 85% of FVIIa 407C was converted into the mono-PEGylated species.

Selective reduction and PEG5k, PEG20k, and PEG40k modification of FVIIa 407C—Thiol modification of FVIIa 407C can be divided into three consecutive steps: (A) a glutaredoxin-catalyzed reduction reaction, (B) thiol-specific alkylation, and (C) purification. At the end of each step, a small aliquot of the reaction mixture was quenched with 10% (v/v) formic acid and analyzed by HPLC as described in material and methods and exemplified in FIG. 7.

(A) FVIIa 407C (4.8 mg) was incubated 4.5 hours at 30° C. in a total volume of 4.4 ml 50 mM HEPES, 100 mM NaCl, 10 mM CaCl$_2$, pH 7.0 buffer containing 0.5 mM GSH, 15 μM GSSG, 25 mM p-aminobenzamidine, and 10 μM Grx2. The initial concentration of GSSG was in the lower end of the optimal working range (shaded area in FIG. 4) to compensate for the formation of GSSG during the reaction. (B) Subsequently, free thiols were modified by addition of PEG5k-maleimide, PEG20k-maleimide, or PEG40k-maleimide (dissolved in water) to a final concentration of 0.8 mM. Thiol alkylation was allowed to proceed for 15 min at room temperature upon quenching with 0.5 mM cysteine. (C) EDTA was added in excess of calcium (20 mM final concentration) and the entire content loaded onto a 1 ml HiTrap Q FF column (Amersham Biosciences, GE Healthcare) equilibrated with buffer A (50 mM HEPES, 100 mM NaCl, 1 mM EDTA, pH 7.0) to capture FVIIa 407C. After wash with buffer A, one-step elution of bound protein was performed with buffer B (10 mM GlyGly, 150 mM NaCl, 10 mM CaCl$_2$, 0.01% Tween 80, pH 7.0) directly onto a HiLoad Superdex 200 16/60 pg column (Amersham Biosciences) mounted in front of the HiTrap column. PEGylated and non-PEGylated species were separated at a flow rate of 1 ml/min and detected by absorption at 280 nm.

Selective reduction and PEG3.4-crosslinking of FVIIa 407C—(A) FVIIa 407C (4.8 mg) was incubated 4.5 hours at 30° C. in a total volume of 4.4 ml 50 mM HEPES, 100 mM NaCl, 10 mM CaCl$_2$, pH 7.0 buffer containing 0.5 mM GSH, 10 μM GSSG, 25 mM p-aminobenzamidine, and 10 μM Grx2. The initial concentration of GSSG was in the lower end of the optimal working range (shaded area in FIG. 4) to compensate for the formation of GSSG during the reaction. (B) EDTA was added in excess of calcium (20 mM final concentration) and the entire content loaded onto a 1 ml HiTrap Q FF column (Amersham Biosciences, GE Healthcare) equilibrated in buffer A (50 mM HEPES, 100 mM NaCl, 1 mM EDTA, pH 7.0) to capture FVIIa 407C. After wash with buffer A to remove unbound glutathione buffer and Grx2p, FVIIa 407C was eluted in one step with buffer B (50 mM HEPES, 100 mM NaCl, 10 mM CaCl$_2$, pH 7.0). The concentration of FVIIa 407C in the eluate was measured by absorbance at 280 nm using an extinction coefficient of $62 \cdot 10^3$ $M^{-1}cm^{-1}$. Cross-linking was performed in the presence of approximately 0.6 equivalent of maleimide-PEG3.4 k-maleimide for 1.5 hours at room temperature. (C) EDTA was added in excess of calcium (20 mM final concentration) and the entire content loaded onto a 1 ml HiTrap Q FF column (Amersham Biosciences, GE Healthcare) equilibrated in buffer A (50 mM HEPES, 100 mM NaCl, 1 mM EDTA, pH 7.0) to capture FVIIa 407C. After wash with buffer A, one-step elution of bound protein was performed with buffer B (10 mM GlyGly, 150 mM NaCl, 10 mM CaCl$_2$, 0.01% Tween 80, pH 7.0) directly onto a HiLoad Superdex 200 16/60 pg column (Amersham Biosciences) to separate PEGylated and non-PEGylated species. The flow rate was 1 ml/min and protein was detected by absorption at 280 nm.

Figure 8:
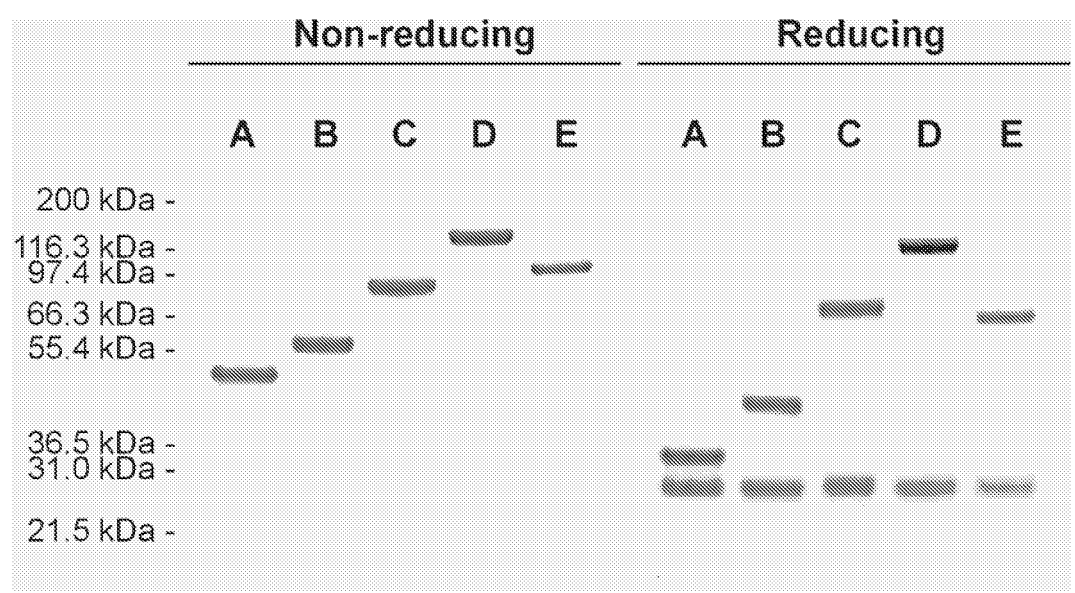
FIG. 8: Reducing (right panel) and non-reducing (left panel) SDS-PAGE analysis of FVIIa 407C (lane A), FVIIa 407C-PEG5k (lane B), FVIIa 407C-PEG20k (lane C), FVIIa 407C-PEG40k (lane D), and FVIIa 407C-PEG3.4 k-FVIIa 407C (lane E).

SDS-PAGE analysis of FVIIa 407C, FVIIa 407C-PEG5k, FVIIa 407C-PEG20k, FVIIa 407C-PEG40k, and FVIIa 407C-PEG3.4 k-FVIIa 407C—FVIIa 407C and 5k, 20k, 40k, and 3.4 k-PEGylated compounds (approx. 1.5 μg of each) were analyzed by reducing and non-reducing SDS-PAGE on a 4-12% Bis-Tris NuPAGE® gel (Invitrogen Life Technologies, Carlsbad, Calif.) run at 200 V for 35 min in MES buffer (Invitrogen Life Technologies, Carlsbad, Calif.) according to manufacturer's recommendations. Gels were washed with water and stained with Simply Blue™ SafeStain (Invitrogen Life Technologies, Carlsbad, Calif.) according to manufacturer's recommendations. Gels are shown in FIG. 8.

Active-site titration of FVIIa 407C, FVIIa 407C-PEG5k, FVIIa 407C-PEG20k, FVIIa 407C-PEG40k, and FVIIa 407C-PEG3.4 k-FVIIa 407C—Active site concentrations of FVIIa 407C and PEGylated compounds were determined from the irreversible loss of amidolytic activity upon titration with sub-stoichiometric levels of d-Phe-Phe-Arg-chloromethyl ketone (FFR-cmk) essentially as described elsewhere (Bock, 1992). Briefly, each protein was diluted into 50 mM HEPES, 100 mM NaCl, 10 mM CaCl$_2$, 0.01% Tween 80, pH 7.0 buffer to an approximate concentration of 300 nM using an extinction coefficient of $62 \cdot 10^3$ $M^{-1}cm^{-1}$ at 280 nm. Diluted protein (20 μl) was then combined with 20 μl 1.5 μM sTF and 20 μl 0-1.2 μM FFR-cmk (freshly prepared in buffer from a FFR-cmk stock dissolved in DMSO and stored at −80° C.). After overnight incubation at room temperature, residual amidolytic activity was measured.

The activity assay was carried out in polystyrene microtiter plates (Nunc, Denmark) in a final volume of 200 μl assay buffer (50 mM HEPES, 100 mM NaCl, 5 mM CaCl$_2$, 0.01% Tween 80, pH 7.4) containing 50 nM sTF and approx. 10 nM FVIIa, corresponding to 10-fold dilutions of the samples. After 15 min pre-incubation at room temperature, 1 mM chromogenic substrate S-2288 was added and the absorbance monitored continuously at 405 nm for 20 min in a Spectra-Max™ 340 microplate spectrophotometer equipped with SOFTmax PRO software (v2.2; Molecular Devices Corp., Sunnyvale, Calif.). Amidolytic activity was reported as the slope of the linear progress curves after blank subtraction. Active site concentrations were determined by extrapolation, as the minimal concentration of FFR-cmk completely abolishing amidolytic activity.

In Table 2 are given the measured active site concentrations relative to the absorbances of the proteins at 280 nm. Values are normalized to 100% for FVIIa 407C.

TABLE 2

Specific active-site concentrations of FVIIa 407C and PEGylated variants. Specific active-site concentrations were measured as the active-site concentration by FFR-cmk titration relative to the absorbance of the protein at 280 nm. Values are normalized to 100% for FVIIa 407C.

| Protein | [Active-site]/$A_{280}$ |
| --- | --- |
| FVIIa 407C | 100% |
| FVIIa 407C-PEG5k | 90% |
| FVIIa 407C-PEG20k | 86% |
| FVIIa 407C-PEG40k | 91% |
| FVIIa 407C-PEG3.4k-FVIIa 407C | 95% |

Figure 9:
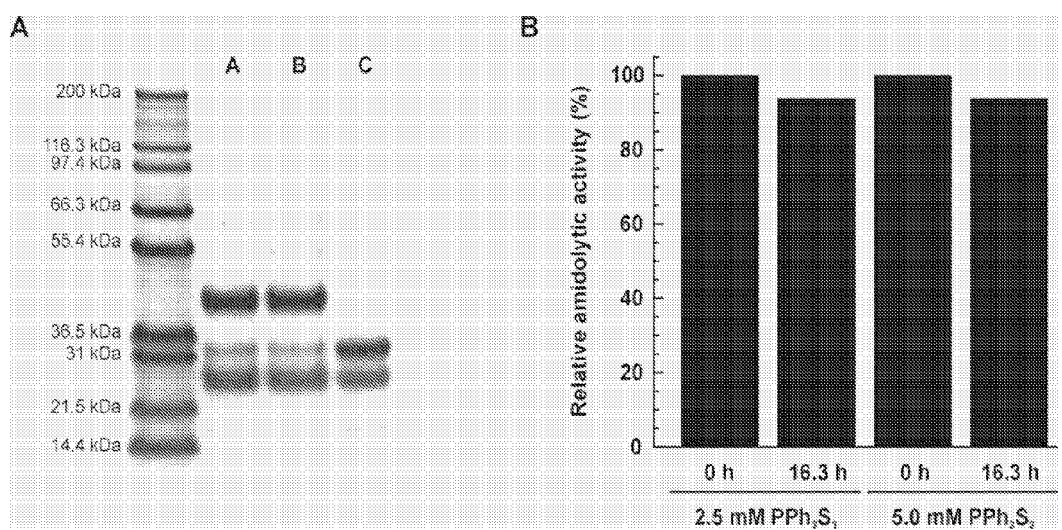
FIG. 9: (A) Reducing SDS-PAGE analysis of FVIIa R396c treated with 2.5 (lane A) or 5.0 mM (lane B) triphenylphosphine-3,3',3" trisulfonic acid (PPh$_3$S$_3$) for 16.3 hrs at room temperature and then labelled with PEG20k-maleimide. Lane C contains untreated FVIIa as a reference. (B) Relative amidolytic activities of FVIIa R396C before (100% activity) and after 16.3 hrs incubation with PPh$_3$S$_3$.

Reduction of FVIIa R396C-mixed disulfides using triphenylphosphine-3,3',3" trisulfonic acid—Small-scale reduction of FVIIa R396C-mixed disulfides using triphenylphosphine-3,3',3" trisulfonic acid ($PPh_3S_3$) was performed as follows: FVIIa R396C (4.4 µM) was treated with either 2.5 or 5.0 mM $PPh_3S_3$ in a total volume of 50 µl reaction buffer (50 mM HEPES, 100 mM NaCl, 10 mM $CaCl_2$, 0.05% Tween 20, pH 7.0) containing 50 mM p-aminobenzamidine. After 16.3 hours incubation at room temperature, reaction mixtures (30 µl) were desalted on Pro●Spin™ Spin columns (Princeton Separations, Adelphia, N.J.) rehydrated in reaction buffer according to manufacturer's instructions to remove excess reductant. Subsequently, free thiols were alkylated with 0.2 mM PEG5k-maleimide for 10 min at room temperature. PEGylated and non-PEGylated FVIIa R396C were separated by reducing SDS-PAGE on a 4-12% Bis-Tris gel (Invitrogen Life Technologies, Carlsbad, Calif.) run at 200 V for 35 min in MES buffer according to manufacturer's recommendations. Gel staining with Simply Blue™ SafeStain (Invitrogen Life Technologies, Carlsbad, Calif.) was performed according to manufacturer's instructions. The gel is shown in FIG. 9A.

The amidolytic activity of FVIIa R396C before and after incubation with $PPh_3S_3$ was measured by 320-fold dilution of the reaction mixture into 200 µl (total volume) 50 mM HEPES, 100 mM NaCl, 5 mM $CaCl_2$, 1 mg/ml BSA, pH 7.4 buffer containing 50 mM sTF. After 15 min pre-incubation at room temperature, 1 mM chromogenic substrate S-2288 was added and the absorbance monitored continuously at 405 nm for 20 min in polystyrene microtiter plates (Nunc, Denmark) using a SpectraMax™ 340 microplate spectrophotometer equipped with SOFTmax PRO software (v2.2; Molecular Devices Corp., Sunnyvale, Calif.). Amidolytic activity was reported as the slope of the linear progress curves after blank subtraction. Results are shown in FIG. 9B.

Selective Reduction of Exposed Disulfides in a Factor VII polypeptide—The commercially available triarylphosphine 1 (trisodium salt of triphenylphosphine-3,3',3"-trisulfonic acid from Aldrich) contains approximately 5% of the corresponding 3,3'-bis-sulfonic acid 2. Thus, 1 was purified by standard reverse-phase HPLC, eluting with a gradient of acetonitrile in water in the presence of 0.1% trifluoroacetic acid.

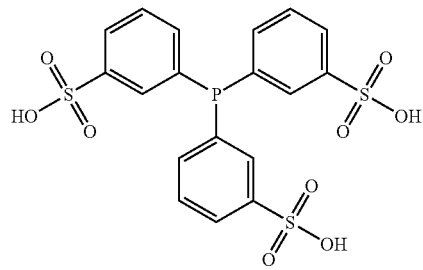

1

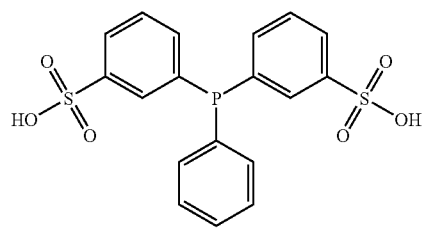

2

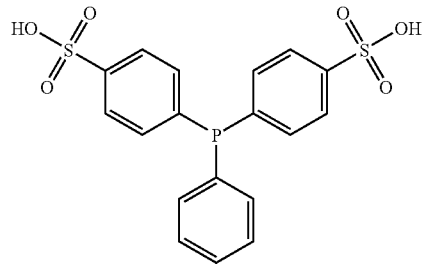

3

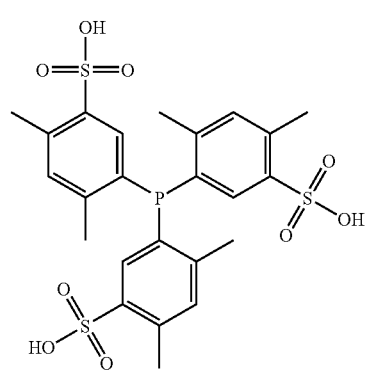

4

It has been shown that triphenylphosphine-3,3',3"-trisulfonic acid (2.5 mM) can be used in conjunction with the active site inhibitor 4-aminobenzamidine to reduce the exposed disulfide bond between glutathione and FVIIa R396C essentially without loss of amidolytic activity. Reductive cleavage of the mixed disulfide bond was demonstrated by subsequent modification of the liberated cysteine with PEG5k-maleimide. Triarylphosphines 1-3 (10 mM) were individually incubated with rFVIIa for 1 h at room temperature. In the presence of 1, rFVIIa retained most of its activity. In contrast, the 3,3'-bis-sulfonic acid 2 caused a rapid decrease in the enzyme's amidolytic activity, much like the analogous 4,4'-bis-sulfonic acid 3 (dipotassium salt from Aldrich), and was therefore not considered optimal for reduction of rFVIIa.

Furthermore, 1 was tested for its ability to reduce cystine dimethyl ester 5. The reaction was conducted at room temperature at 15 mM concentration of 1 in water. The substrate was present at 5 mM concentration. It was demonstrated by LC-MS analyses that the disulfide bond in 5 was reduced under the given conditions.

Scheme 1

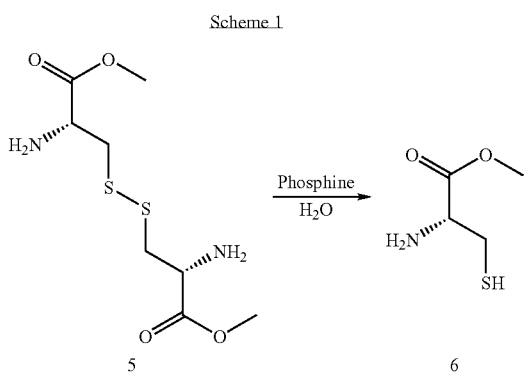

The more sterically hindered triarylphosphine 4 (trisodium salt from Strem) was found to be almost unreactive towards rfVIIa, suggesting the feasibility of developing a more selective reducing agent. Compounds 9-11 represent non-limiting examples of triarylphosphines which are expected to be selective disulfide reducing agents.

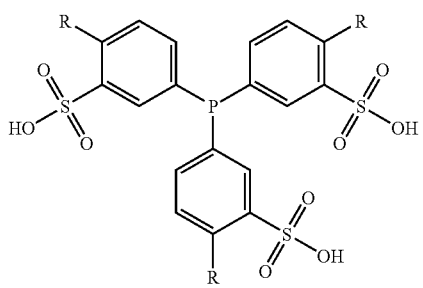

R = H, Me, Et, Pr, 2-Pr, Bu,
MeO, EtO, PrO, 2-PrO, BuO.

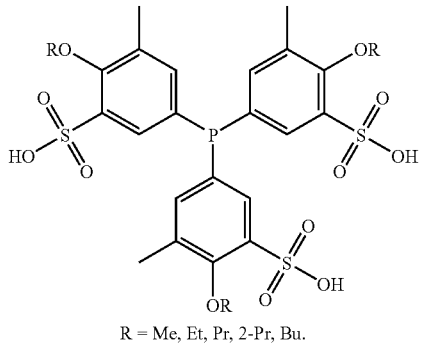

R = Me, Et, Pr, 2-Pr, Bu.

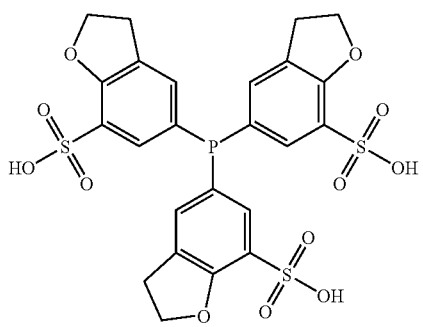

REFERENCES

Bock, P. E. (1992). Active-site-selective labeling of blood coagulation proteinases with fluorescence probes by the use of thioester peptide chloromethyl ketones. I. Specificity of thrombin labeling. J. Biol Chem 267, 14963-14973.

Chau, M. H. and Nelson, J. W. (1991). Direct measurement of the equilibrium between glutathione and dithiothreitol by high performance liquid chromatography. FEBS Lett. 291, 296-298.

Fernandes, A. P. and Holmgren, A. (2004) Glutaredoxins: glutathione-dependent redox enzymes with functions far beyond a simple thioredoxin backup system. Antioxid.Redox.Signal., 6, 63-74.

Freskgard, P. O., Olsen, O. H., and Persson, E. (1996). Structural changes in factor VIIa induced by Ca2+ and tissue factor studied using circular dichroism spectroscopy. Protein Sci 5, 1531-1540.

Gilbert, H. F. (1995). Thiol/disulfide exchange equilibria and disulfide bond stability. Methods Enzymol. 251, 8-28.

Grant, C. (2001). MicroReview: Role of the glutathione/glutaredoxin and thioredoxin systems in yeast growth and response to stress conditions. Mol. Microbiol. 39, 533-541.

Grimberg, J., Maguire, S., and Belluscio, L. (1989). A simple method for the preparation of plasmid and chromosomal E. coli DNA. Nucleic Acids Res 17, 8893.

Higashi, S., Matsumoto, N., and Iwanaga, S. (1997). Conformation of factor VIIa stabilized by a labile disulfide bond (Cys-310-Cys-329) in the protease domain is essential for interaction with tissue factor. J. Biol. Chem. 272, 25724-25730.

Holmgren, A., Aslund, F. (1995) Glutaredoxin, Method Enzymol. 252, 283-292

Hoffman, C. S, and Winston, F. (1987). A ten-minute DNA preparation from yeast efficiently releases autonomous plasmids for transformation of Escherichia coli. Gene 57, 267-272.

Loferer, H., Wunderlich, M., Hennecke, H., and Glockshuber, R. (1995). A bacterial thioredoxin-like protein that is exposed to the periplasm has redox properties comparable with those of cytoplasmic thioredoxins. J. Biol. Chem. 270, 26178-26183.

Luikenhuis, S., Perrone, G., Dawes, I. W., and Grant, C. M. (1998). The yeast Saccharomyces cerevisiae contains two glutaredoxin genes that are required for protection against reactive oxygen species. Mol. Biol. Cell 9, 1081-1091.

Lundberg, M., Johansson, C., Chandra, J., Enoksson, M., Jacobsson, G., Ljung, J., Johansson, M., and Holmgren, A. (2001). Cloning and expression of a novel human glutaredoxin (Grx2) with mitochondrial and nuclear isoforms. 3 Biol Chem 276, 26269-26275

Rodriguez-Manzaneque, M. T., Ros, J., Cabiscol, E., Sorribas, A., and Herrero, E. (1999). Grx5 glutaredoxin plays a central role in protection against protein oxidative damage in Saccharomyces cerevisiae. Mol Cell Biol 19, 8180-8190.

Oe, T., Ohyagi, T., Naganuma, A. (1998) Determination of γ-glutamylglutathione and other low-molecular-mass thiol compounds by isocratic high-performance liquid chromatography with fluorimetric detection. J. Chrom. B, 708, 285-289.

Ostergaard, H., Tachibana, C., and Winther, J. R. (2004). Monitoring disulfide bond formation in the eukaryotic cytosol. J Cell Biol 166, 337-345.

Padilla, C. A., Martinez-Galisteo, E., Barcena, J. A., Spyrou, G., and Holmgren, A. (1995). Purification from placenta, amino acid sequence, structure comparisons and cDNA cloning of human glutaredoxin. Eur J Biochem 227, 27-34.

Persson, E., Bak, H., Ostergaard, A., and Olsen, O. H. (2004). Augmented intrinsic activity of Factor VIIa by replacement of residues 305, 314, 337 and 374: evidence of two unique mutational mechanisms of activity enhancement. Biochem J 379, 497-503.

Persson, E. and Nielsen, L. S. (1996). Site-directed mutagenesis but not gamma-carboxylation of Glu-35 in factor VIIa affects the association with tissue factor. FEBS Lett 385, 241-243.

Riddles, P. W., Blakeley, R. L., and Zerner, B. (1979). Ellman's reagent: 5,5'-dithiobis(2-nitrobenzoic acid)—a reexamination. Anal. Biochem. 94, 75-81.

Sambrook, J., Fritsch, E. F., and Maniatis, T. (1989). Molecular Cloning: A Laboratory Manual. (Cold Spring Harbor, N.Y.: Cold Spring Harbor Laboratory).

Sichler, K., Banner, D. W., D'Arcy, A., Hopfner, K. P., Huber, R., Bode, W., Kresse, G. B., Kopetzki, E., and Brandstetter, H. (2002). Crystal structures of uninhibited factor VIIa link its cofactor and substrate-assisted activation to specific interactions. J. Mol. Biol. 322, 591-603. Takahashi, N. and Creighton, T. E. (1996). On the reactivity and ionization of the active site cysteine residues of *Escherichia coli* thioredoxin. Biochemistry 35, 8342-8353.

Thim, L., Bjoern, S., Christensen, M., Nicolaisen, E. M., Lund-Hansen, T., Pedersen, A. H., and Hedner, U. (1988). Amino acid sequence and posttranslational modifications of human factor VIIa from plasma and transfected baby hamster kidney cells. Biochemistry 27, 7785-7793.

Wang, E. C. W., Hung, S.-H., Cahoon, M., Hedstrom, L. (1997) The role of Cys191-Cys220 disulfide bond in trypsin: new targets for engineering substrate specificity. Protein Engineering, 10, 405-411.

Yang, Y., Jao, S., Nanduri, S., Starke, D. W., Mieyal, J. J., and Qin, J. (1998). Reactivity of the human thioltransferase (glutaredoxin) C7S, C25S, C78S, C82S mutant and NMR solution structure of its glutathionyl mixed disulfide intermediate reflect catalytic specificity. Biochemistry 37, 17145-17156.

SEQ ID NO:1: GGGCCGCCCATATGGTATCTCAAGAAACTATC

SEQ ID NO:2: GCCCGGGCTCGAGATTTGCAAGAATAGGTTCTAAC

SEQ ID NO:3: GCCGCCGGCATATGAAGCTATACATTTACGATCACTGCCC

SEQ ID NO:4: CCGCCGCCCTCGAGAATCGCCATTGATGATAACAAATTGATTTGTG

SEQ ID NO:5: GTTTAGGGCTGCATGCGAGTATGGACAGTACG

SEQ ID NO:6: CGTACTGTCCATACTCGCATGCAGCCCTAAAC

---

The invention claimed is:

1. A method for selective reduction of an engineered protein in its active conformation comprising at least one non-native cysteine, said protein comprising one or more cysteine moieties conjugated through a disulfide bridge to a low-molecular weight thiol (RS-Cys), said moiety/moieties not being involved in intramolecular S—S bridges (Cys-S—S-Cys) when the protein is in its active form, the method comprising the step of allowing the low-molecular weight thiol-conjugated protein to react with a mixture comprising a redox buffer under non-denaturing conditions, wherein the redox buffer is a redox pair of reduced and oxidized glutathione, the concentration of the reduced glutathione is in the range of 0.01-50 mM, and the concentration of the oxidized glutathione is in the range of 0.001-2 mM, and wherein the engineered protein is a Factor VII polypeptide.

2. The method according to claim 1, wherein the mixture further comprises a glutaredoxin thiol/disulfide redox catalyst selected from the group consisting of *Escherichia coli* Grx1, *Escherichia coli* Grx2, or *Escherichia coli* Grx3, *Saccharomyces cerevisiae* Grx1p, *Saccharomyces cerevisiae* Grx2p, *Saccharomyces cerevisiae* Grx3p, *Saccharomyces cerevisiae* Grx4p, and *Saccharomyces cerevisiae* Grx5p, *Homo sapiens* Grx1 and *Homo sapiens* Grx2.

3. The method according to any claim 2, wherein the redox catalyst is used in a concentration of 0.001-20μM.

4. The method according to claim 1, wherein the mixture does not comprise a protein disulfide isomerase (PDI).

5. The method according to claim 1, wherein the mixture further comprises an inhibitor of the protein.

6. The method according to claim 1, wherein said engineered protein has one or more intramolecular S—S bridges (Cys-S—S-Cys).

7. The method according to claim 1, wherein said engineered protein has one or more intermolecular S—S bridges (Cys-S—S-Cys) with another engineered protein.

8. The method according to claim 1, wherein said engineered protein is a protein with labile disulfide bonds.

9. The method according to claim 1, wherein the method comprises the simultaneous and/or subsequent step of conjugating at least one of the selectively reduced cysteine (HS-Cys) moieties with a chemical group.

10. The method according to claim 9, wherein the chemical group is a polyethylene glycol (PEG).

11. The method according to claim 10, wherein the chemical group is a polyethyleneglycol having an average molecular weight of in the range of 500-100,000.

12. A method for selective reduction of a Factor VII polypeptide in its active conformation, said Factor VII polypeptide comprising one or more one or more cysteine moieties conjugated through a disulfide bridge to a low-molecular weight thiol (RS-Cys), said moiety/moieties not being involved in intramolecular S—S bridges (Cys-S—S-Cys) when the FVII polypeptide is in its active form, the method comprising the step of allowing the low-molecular weight thiol-conjugated Factor VII polypeptide to react with a mixture comprising reduced and oxidized glutathione and a glutaredoxin, and the simultaneous and/or subsequent step of conjugating at least one of the selectively reduced cysteine (HS-Cys) moieties with a chemical group, each step under non-denaturing conditions.

* * * * *